(12) United States Patent
Burnet et al.

(10) Patent No.: US 9,416,123 B2
(45) Date of Patent: Aug. 16, 2016

(54) KINASE MODULATORS FOR THE TREATMENT OF CANCER

(71) Applicant: Synovo GmbH, Tubingen (DE)

(72) Inventors: Michael William Burnet, Tubingen (DE); Bassam Abu Thaher, Khan Younis (PS); Jan Ehlert, Ehrenkirchen (DE); Michael Kubbutat, Schallstadt (DE); Christoph Schaechtele, Freiburg (DE); Frank Totzke, Freiburg (DE)

(73) Assignee: Synovo GmbH, Tubingen (DE)

( * ) Notice: Subject to any disclaimer, the term of this patent is extended or adjusted under 35 U.S.C. 154(b) by 0 days.

(21) Appl. No.: 14/229,798

(22) Filed: Mar. 28, 2014

(65) Prior Publication Data

US 2014/0336225 A1    Nov. 13, 2014

Related U.S. Application Data

(63) Continuation of application No. PCT/IB2012/002387, filed on Oct. 1, 2012.

(60) Provisional application No. 61/541,648, filed on Sep. 30, 2011.

(51) Int. Cl.
*C07D 401/04*    (2006.01)

(52) U.S. Cl.
CPC .................. *C07D 401/04* (2013.01)

(58) Field of Classification Search
CPC .................................................. C07D 401/04
USPC ............. 546/276.1, 256, 275.4; 514/341, 333
See application file for complete search history.

(56) References Cited

U.S. PATENT DOCUMENTS

| 5,750,550 A | 5/1998 | Eissenstat et al. |
| 6,914,069 B2 * | 7/2005 | Shroff et al. .................. 514/341 |
| 2008/0207699 A1 | 8/2008 | Hoelzemann et al. |

FOREIGN PATENT DOCUMENTS

| BE | 612971 A1 | 7/1962 |
| BE | 655242 A | 5/1965 |
| WO | WO-2007/027842 A1 | 3/2007 |

OTHER PUBLICATIONS

Moskalenko et al., "Synthesis of, etc.," CA 64:104263 (1966).*
Thaher et al., "Tri-and Tetrasubstituted Pyrazole Derivates: Regioisomerism Switches Activity from p38MAP Kinase to Important Cancer Kinases", Journal of Medicinal Chemistry, vol. 55, No. 2, pp. 961-965 (2012).
Aly et al., "A convenient synthesis of some pyrazolinone and pyrazole derivatives", Journal of the Chinese Chemical Society, vol. 51, No. 5A, pp. 983-990 (2004).
International Search Report and Written Opinion mailed Feb. 25, 2013, in corresponding PCT Application No. PCT/IB2012/002387.

* cited by examiner

*Primary Examiner* — Patricia L Morris
(74) *Attorney, Agent, or Firm* — Wolf, Greenfield & Sacks, P.C.

(57) ABSTRACT

Compounds of the substituted pyrazole class as treatments for cancer are reported. A method of treating cancer in which a compound that inhibits the activity of receptor kinases. Said method is effective and can be provided in addition to standard therapies, notably chemotherapy using cytotoxic drugs and other forms of immune therapy including therapeutic vaccines.

6 Claims, 6 Drawing Sheets

Scheme 1. General methods for pyrazole synthesis

KINASE MODULATORS FOR THE TREATMENT OF CANCER

RELATED APPLICATIONS

This application is a continuation of PCT Patent Application No. PCT/IB2012/002387, filed Oct. 1, 2012, which claims the benefit of and priority to U.S. Provisional Patent Application Ser. No. 61/541,648, filed Sep. 30, 2011. The contents of each of the foregoing applications are incorporated herein by reference in their entirety.

BACKGROUND OF THE INVENTION

The treatment of disease via the inhibition of growth factors, their receptors and the regulatory systems associated with them is an established therapy concept. That cancers adapt to these treatments, or express mutant receptors that are not bound by standard ligands means that it is advantageous to treat cancer patients with a variety of such inhibitors in order to broaden spectrum and maintain inhibition of tumour growth.

Epidermal growth factor is an example of a growth regulator that is disregulated in certain diseases such as lung cancer and amyloid related dementias.

Various inhibitors of this growth factor and its receptors are known and have utility in treating certain forms of cancer, albeit limited to those that express specific mutant forms of the target. Clearly, in the context of a variable tumour, a substance that inhibits multiple mutant forms of this target would be preferable to an agent that inhibits specifically only one mutation. Similarly, although tumours may express a mutant form of growth factor receptor, they may also express or over-express multiple growth factor receptors that together confer the capacity for over-growth. A compound that exerts inhibition of multiple receptors is, therefore, more generally or widely applicable than one that inhibits only one receptor type.

While inhibition of growth stimulation is a desirable goal in cancer therapy, elimination of the tumour itself requires either a substance that causes tumour cells to die, or one that promotes immune action on the tumour.

One means of achieving this objective is to select molecules that are ligands to the key signaling proteins of tumours that suppress local immune response. It is known, for example, that preventing tumours or their stromal cells from secreting IL-10 is an effective means of activating Natural Killer and T-cells in the tumour environment. A ligand of moderate potency to a MAP kinase can have this effect.

Similarly, many tumours are dependant on hormone related signaling. Inhibition of hormone signal processing is a valid means of suppressing growth or inducing apoptosis. Androgen processing in particular is a potent factor in prostate cancer. Androgen processing receptor kinases are, therefore, also relevant cancer targets.

SUMMARY

The invention relates to compounds that act by means of inhibiting the action of protein kinases, growth factors, their receptors and related functions. The compounds may be administered to patients in need by standard means. The compounds are distinguished by possessing a diazole ring core with an amine side-chain and multiple aromatic substituents.

DETAILED DESCRIPTION OF THE INVENTION

Technical Problem

Treatments for cancer are commonly cytotoxic and to reduce toxicity, it has been proposed to develop compounds that bind only to targets specifically up-regulated in cancers and ideally only the variants of those targets that are mutated in cancers. By testing compounds for their ability to specifically inhibit such targets, it is possible to identify compounds potentially active in cancer. The problem to solve is that many cancers have highly plastic genomes and any agent exerting a specific selection pressure is quickly overcome by adaptive mutations. What is needed is a substance that suppresses multiple growth promoting pathways in tumours, i.e. exerts no specific selection pressure, and also possesses the means to prevent tumour defense responses, or promote immune response to the incapacitated tumour.

Solution to Problem

The compounds reported here are simple to synthesise and yet maintain general binding activity to key growth promoting tumour receptors. In particular they bind to both Epidermal Growth Factor Receptors (including EGF-R L858R) as well as PCK types. Finally, they are potent ligands to Androgen processing kinases (ACK1), making them potentially suitable for use in androgen promoted cancers. The observation that EGF-R is linked to Alzheimer's disease (Li et al, 2007, Lei et al., 2012, and Retello et al, 2007) raises the prospect that said compounds may be useful also in certain Dementias and Amyloidoses.

Advantageous Effects of Invention

The compounds reported here are useful in many respects. They are ligands to key growth regulators and tumour defense regulators. They are simple to synthesise, stable and active in vivo.

Figure 1:
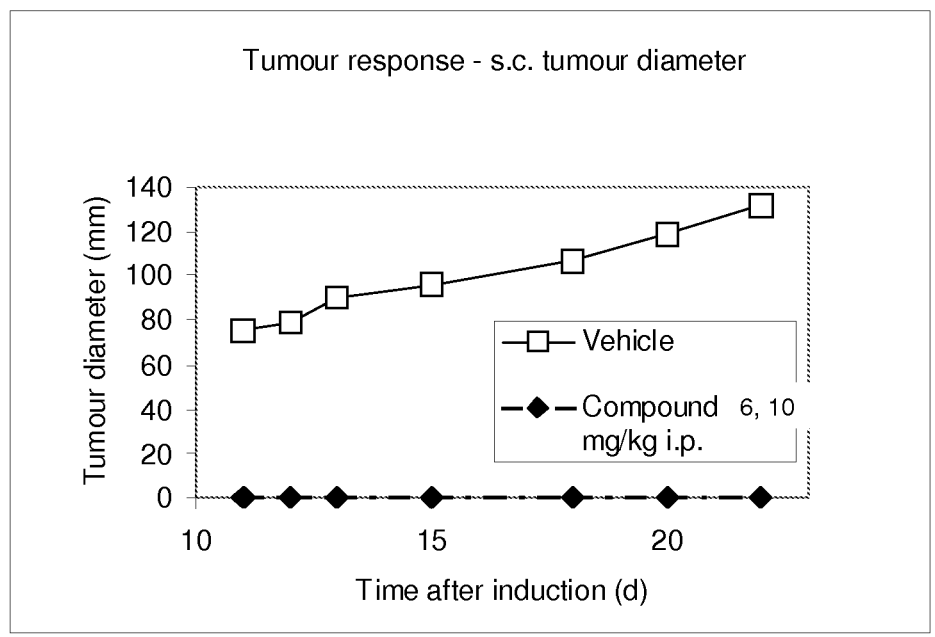
FIG. 1 Growth of subcutaneous tumours in mice in which 50000 3LL lung carcinoma cells have been placed under the skin on the flank at day 1. Data are the mean of 8 animals (Compound 2) and 12 animals (Vehicle).

The invention now will be described more fully hereinafter through reference to various embodiments. These embodiments are provided so that this disclosure will be thorough and complete, and will fully convey the scope of the invention to those skilled in the art. Indeed, the invention may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise. The present invention is directed to compounds, pharmaceutical compositions providing the combounds, and methods of using the combinations and compositions for treating cancer and inflammatory diseases.

Definitions

The term "compound" as used herein means a chemical entity, whether in a crude mixture or purified and isolated The term "TNF" shall mean any member of the Tumour necrosis factor super family. The term "TNFa" shall mean Tumour Necrosis Factor alpha from any applicable species including murine and human forms.

The term "alkyl" as used herein means saturated straight, branched, or cyclic hydrocarbon groups. In particular embodiments, alkyl refers to groups comprising 1 to 10 carbon atoms ("C1-10 alkyl"). In further embodiments, alkyl refers to groups comprising 1 to 8 carbon atoms ("C1-8 alkyl"), 1 to 6 carbon atoms ("C1-6 alkyl"), or 1 to 4 carbon atoms ("C1-4 alkyl"). In specific embodiments, alkyl refers to methyl, trifluoromethyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. Substituted alkyl refers to alkyl substituted with one or more non-interfering substituents, such as but not limited to halo (e.g., Cl, F, Br, and I); halogenated alkyl (e.g., CF3, 2-Brethyl, CH2F, CH2Cl, CH2CF3, or CF2CF3); hydroxyl; amino; carboxylate; carboxamido; alkylamino; arylamino; alkoxy; aryl; aryloxy; nitro; cycloalkyl; acetylene; alkanoyloxy; ketone; azido; cyano; thio; sulfonic acid; sulfate; phosphonic acid; phosphate; and phosphonate.

The term "alkenyl" as used herein means alkyl moieties wherein at least one saturated C—C bond is replaced by a double bond. In particular embodiments, alkenyl refers to groups comprising 1 to 10 carbon atoms ("C1-10 alkenyl"). In further embodiments, alkyl refers to groups comprising 1 to 8 carbon atoms ("C1-8 alkenyl"), 1 to 6 carbon atoms ("C1-6 alkenyl"), or 1 to 4 carbon atoms ("C1-4 alkenyl"). In specific embodiments, alkenyl can be vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, or 5-hexenyl.

The term "alkynyl" as used herein means alkyl moieties wherein at least one saturated C—C bond is replaced by a triple bond. In particular embodiments, alkynyl refers to groups comprising 1 to 10 carbon atoms ("C1-10 alkynyl"). In further embodiments, alkyl refers to groups comprising 1 to 8 carbon atoms ("C1-8 alkynyl"), 1 to 6 carbon atoms ("C1-6 alkynyl"), or 1 to 4 carbon atoms ("C1-4 alkynyl"). In specific embodiments, alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl.

The term "alkoxy" as used herein means straight or branched chain alkyl groups linked by an oxygen atom (i.e., —O-alkyl or -alkyl-O-alkyl), wherein alkyl is as described above. In particular embodiments, alkoxy refers to oxygen-linked groups comprising 1 to 10 carbon atoms ("C1-10 alkoxy"). In further embodiments, alkoxy refers to oxygen-linked groups comprising 1 to 8 carbon atoms ("C1-8 alkoxy"), 1 to 6 carbon atoms ("C1-6 alkoxy"), or 1 to 4 carbon atoms ("C1-4 alkoxy"). The term "halo" or "halogen" as used herein means fluorine, chlorine, bromine, or iodine.

The term "heterocycle" or "heterocyclic" as used herein means one or more rings of 5, 6 or 7 atoms with or without unsaturation or aromatic character and having at least one ring atom which is not carbon. Preferred heteroatoms include sulfur, oxygen, and nitrogen. Multiple rings may be fused, as in quinoline or benzofuran. "Substituted heterocycle" is heterocycle having one or more side chains formed from non-interfering substituents.

The term "aryl" as used herein means a stable monocyclic, bicyclic, or tricyclic carbon ring of up to 8 members in each ring, wherein at least one ring is aromatic as defined by the Huckel 4n+2 rule. Multiple aryl rings may be fused, and aryl rings may be fused or unfused with one or more cyclic hydrocarbon, heteroaryl, or heterocyclic rings. Exemplary aryl groups according to the invention include phenyl, naphthyl, tetrahydronaphthyl, and biphenyl. The aryl group can be substituted with one or more non-interfering substituents, such as, for example, hydroxyl, amino, alkylamino, arylamino, alkoxy, aryloxy, nitro, cyano, sulfonic acid, sulfate, phosphonic acid, phosphate, or phosphonate.

The term "heteroaryl" as used herein means an aryl group containing from one or more (particularly one to four) non-carbon atom(s) (particularly N, O, or S) or a combination thereof, which heteroaryl group is optionally substituted at one or more carbon or nitrogen atom(s) with alkyl, —CF3, phenyl, benzyl, or thienyl, or a carbon atom in the heteroaryl group together with an oxygen atom form a carbonyl group, or which heteroaryl group is optionally fused with a phenyl ring. Heteroaryl rings may also be fused with one or more cyclic hydrocarbon, heterocyclic, aryl, or heteroaryl rings. Heteroaryl includes, but is not limited to, 5-membered heteroaryls having one hetero atom (e.g., thiophenes, pyrroles, furans); 5 membered heteroaryls having two heteroatoms in 1, 2 or 1,3 positions (e.g., oxazoles, pyrazoles, imidazoles, thiazoles, purines); 5-membered heteroaryls having three heteroatoms (e.g., triazoles, thiadiazoles); 5-membered heteroaryls having 3 heteroatoms; 6-membered heteroaryls with one heteroatom (e.g., pyridine, quinoline, isoquinoline, phenanthrine, 5,6-cycloheptenopyridine); 6-membered heteroaryls with two heteroatoms (e.g., pyridazines, cinnolines, phthalazines, pyrazines, pyrimidines, quinazolines); 6-membered heretoaryls with three heteroatoms (e.g., 1,3,5-triazine); and 6-membered heteroaryls with four heteroatoms. Substituted heteroaryl is heteroaryl having one or more non-interfering groups as substituents.

The terms "aralkyl" and "arylalkyl" as used herein mean an aryl group as defined above linked to the molecule through an alkyl group as defined above.

The terms "alkaryl" and "alkylaryl" as used herein means an alkyl group as defined above linked to the molecule through an aryl group as defined above.

The term "acyl" as used herein means a carboxylic acid ester in which the non-carbonyl moiety of the ester group is selected from straight, branched, or cyclic alkyl or lower alkyl; alkoxyalkyl including methoxymethyl; aralkyl including benzyl; aryloxyalkyl such as phenoxymethyl; aryl including phenyl optionally substituted with one or more non-interfering substituents, such as halogen, C1-C6 alkyl or C1-Ce alkoxy; sulfonate esters such as alkyl or aralkyl sulphonyl including methanesulfonyl; mono-, di-, or triphosphate ester; trityl or monomethoxytrityl; substituted benzyl; trialkylsilyl such as dimethyl-t-butylsilyl or diphenylmethylsilyl. Aryl groups in the esters optimally comprise a phenyl group.

The term "amino" as used herein means a moiety represented by the structure NR2, and includes primary amines, and secondary and tertiary amines substituted by alkyl (i.e., alkylamino). Thus, R2 may represent two hydrogen atoms, two alkyl moieties, or one hydrogen atom and one alkyl moiety.

The terms "alkylamino" and "arylamino" as used herein mean an amino group that has one or two alkyl or aryl substituents, respectively.

The term "non-interfering substituents" as used herein means any groups that yield stable compounds. Suitable non-interfering substituents or radicals include, but are not limited to, halo, C1-C10 alkyl, C2-C10 alkenyl, C2-C10 alkynyl, C1-C10 alkoxy, C7-C12 aralkyl, C7-C12 alkaryl, C3-C10 cycloalkyl, C3-C10 cycloalkenyl, phenyl, substituted phenyl, toluoyl, xylenyl, biphenyl, C2-C12 alkoxyalkyl, C7-C12 alkoxyaryl, C7-C12 aryloxyalkyl, C0-C12 oxyaryl, C1-Ce alkylsulfinyl, C1-C10 alkylsulfonyl, —(CH2)D1-O-(C1-C10 alkyl) wherein m is from 1 to 8, aryl, substituted aryl, substituted alkoxy, fluoroalkyl, heterocyclic radical, substituted heterocyclic radical, nitroalkyl, —NO2, —CN, —NRC(O)—(C1-C10 alkyl), —C(O)—(C1-C10 alkyl), C2-C10 thioalkyl, —C(O)O— (C1-C10 alkyl), —OH, —SO2, =S, —COOH, —NR2, carbonyl, —C(O)—(C1-C10 alkyl)-CF3, —C(O)—CF3, —C(O)NR2, —(C1-C10 alkyl)-S—(C6-C12 aryl), —C(O)—(C6-C12 aryl), —(CH2) m-0-(CH2)m-0-(C1-C10 alkyl) wherein each m is from 1 to 8, —C(O)NR2, —C(S)NR2, —SO2NR2, —NRC(O)NR2, —NRC(S)NR2, salts thereof, and the like. Each R as used herein is H, alkyl or substituted alkyl, aryl or substituted aryl, aralkyl, or alkaryl.

The term "analogue" as used herein means a compound in which one or more individual atoms or functional groups have been replaced, either with a different atom or a different functional, generally giving rise to a compound with similar properties. The term "derivative" as used herein means a compound that is formed from a similar, beginning compound by attaching another molecule or atom to the beginning compound. Further, derivatives, according to the invention, encompass one or more compounds formed from a precursor compound through addition of one or more atoms or molecules or through combining two or more precursor compounds. The term "prodrug" as used herein means any compound which, when administered to a mammal, is converted in whole or in part to a compound of the invention. The term "active metabolite" as used herein means a physiologically active compound that results from the metabolism of a compound of the invention, or a prodrug thereof, when such compound or prodrug is administered to a mammal.

The term "intermittent administration" as used herein means administration of a therapeutically effective dose of a composition according to the invention, followed by a time period of discontinuance, which is then followed by another administration of a therapeutically effective dose, and so forth.

"Pharmaceutically acceptable excipient" or "pharmaceutically acceptable carrier" refers to an excipient that can be included in the compositions of the invention and that causes no significant adverse toxicological effects to the patient. "Pharmacologically effective amount," "physiologically effective amount," "therapeutically effective amount", and "therapeutically effective dose" are used interchangeably herein to mean the amount of a conjugate of the invention present in a pharmaceutical preparation that is needed to provide a desired level of active agent and/or conjugate in the bloodstream or in the target tissue. The precise amount will depend upon numerous factors, e.g., the particular active agent, the components and physical characteristics of the pharmaceutical preparation, intended patient population, patient considerations, and the like, and can readily be determined by one skilled in the art, based upon the information provided herein and available in the relevant literature. The term "antiproliferative agent" as used herein means a compound that decreases the hyperproliferation of cells. The term "abnormal cell proliferation" as used herein means a disease or condition characterized by the inappropriate growth or multiplication of one or more cell types relative to the growth of that cell type or types in an individual not suffering from that disease or condition. The term "cancer" as used herein means a disease or condition characterized by uncontrolled, abnormal growth of cells, which can spread locally or through the bloodstream and lymphatic system to other parts of the body. The term includes both tumor-forming or non-tumor forming cancers, and includes various types of cancers, such as primary tumors and tumor metastasis. The term "tumor" as used herein means an abnormal mass of cells within a multicellular organism that results from excessive cell division that is uncontrolled and progressive, also called a neoplasm.

It has been discovered according to the present invention that compounds active on multiple growth factor receptor kinases (see example 25) can be useful in the treatment of cancer (see example 24). In a preferred embodiment, the kinase inhibitor has the structure according to Formula 1 wherein:

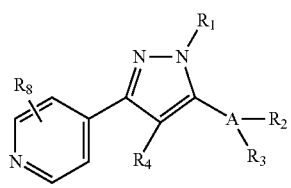

Formula 1

$R_1$=is a cyclic or bicyclic system with 3 to 10 carbon atoms with 0 to 4 substituents selected from alkyls of 1 to 5 carbons, alkylidene groups (C4), halogens, nitryls, ethers, nitros;

A is N or O;

When A=O, $R_2$ is no atom, and $R_3$ is as defined below (for the purposes of clarity, an OH in this position would be A=O, R3=H, R2 not present);

When A=N, $R_2$ and $R_3$ are independently selected from hydrogen, methyl, ethyl, isopropyl, sec-butyl, isobutyl, tert-butyl, 2-(3-methyl)butyl, cyclopropyl, cyclobutyl, cyclopentyl, cyclohexyl, morpholinyl, methylcyclohexyl, methylcyclopentyl, methylmorpholinyl, hydroxycyclohexyl, hydroxycyclopentyl, benzyl, 1-phenylethyl tetrahydropyran-4-yl, (4-hydroxy)cyclohexyl, 1-(1-phenyl)propyl1-indanyl, 1-(1,2,3,4-tetrahydro)naphthyl, 1-(2-phenyl)propyl, 1-(1-methyl-3-phenyl)propyl_1,2-diphenylethyl, 1,3-diphenyl-2-propyl, (4-tert-butyl)benzyl4-fluorobenzyl, 2-(2-para-xylyl)ethyl, (1-naphthyl)methyl, (2-thiophenyl)methyl, 2-(2-thiophenyl)ethyl, (2-benzo[b]t2-furyl)methyl, [(5-methyl)furan-2-yl]-methyl, (2-pyridyl)methyl, (3-pyridyl)methyl, (4-pyridyl)methyl;

$R_4$=H, alkyl, carboxyl, carboxymethyl, carboxyethyl, nitrile, amido, an aromatic system with 0 to 3 substituents selected from, Cl, Br, I, F, $CF_3$, $OCF_3$;

or $R_3$=$R_4$ and is selected from carbonyl, —(C=O)—$NR_{10}$—(C=O)—, wherein $R_{10}$ is selected from H, methyl, ethyl;

$R_8$=H, $NHR_9$, alkyl;

$R_9$=methyl, ethyl, isopropyl, sec-butyl, Isobutyl, tert-butyl, 2-(3-methyl)butyl, cyclopropyl, cyclobutyl, cyclopentyl, cyclohexyl, morpholinyl, methylcyclmethylcyclopentyl, methylmorpholinyl, hydroxycyclohexylhydroxycyclopentyl, benzyl1-phenylethyl, tetrahydropyran-4-yl, (4-hydroxy)cyclohexyl, 1-(1-phenyl)propyl, 1-indanyl, 1-(1,2,3,4-tetrahydro)naphthyl, 1-(2-phenyl)propyl, 1-(1-methyl-3-phenyl)propyl, 1,2-diphenylethyl, 1,3-diphenyl-2-propyl, (4-tert-butyl)benzyl, 4-fluorobenzyl, 2-(2-para-xylyl)ethyl, (1-naphthyl)methyl, (2-thiophenyl)methyl, 2-(2-thiophenyl)ethyl, (2-benzo[b]thiopheneyl)methyl, (2-furyl)methyl, [(5-methyl)furan-2-yl]-methyl, (2-pyridyl)methyl, (3-pyridyl)methyl, (4-pyridyl)methyl.

In further preferred embodiment, $R_1$ is an aromatic system with 5 or 6 ring members 0 to 3 substituents selected from alkyls of 1 to 5 carbons, alkylidene groups (C4), halogens, nitryls, ethers, nitros.

In another preferred embodiment, $R_4$ is an aromatic system with 5 or 6 ring members 0 to 3 substituents selected from alkyls of 1 to 5 carbons, alkylidene groups (C4), halogens, nitryls, ethers, nitros.

In a still further preferred embodiment, $R_4$ is 4-Fluorophenyl and R1 is 2,4,6-trichlorophenyl.

In another embodiment, the invention provides a compound according to Formula 3 wherein:

Formula 3

$R_1$=is a cyclic or bicyclic system with 3 to 10 carbon atoms with 0 to 4 substituents selected from alkyls of 1 to 5 carbons, alkylidene groups (C4), halogens, nitryls, ethers, nitros;

$R_2$ is independently selected from hydrogen, methyl, ethyl, isopropyl, sec-butyl
isobutyl
tert-butyl
2-(3-methyl)butyl
cyclopropyl
cyclobutyl
cyclopentyl
cyclohexyl
morpholinyl
methylcyclohexyl
methylcyclopentyl
methylmorpholinyl
hydroxycyclohexyl
hydroxycyclopentyl
benzyl
1-phenylethyl
tetrahydropyran-4-yl
(4-hydroxy)cyclohexyl
1-(1-phenyl)propyl
1-indanyl
1-(1,2,3,4-tetrahydro)naphthyl
1-(2-phenyl)propyl
1-(1-methyl-3-phenyl)propyl
1,2-diphenylethyl
1,3-diphenyl-2-propyl
(4-tert-butyl)benzyl
4-fluorobenzyl
2-(2-para-xylyl)ethyl
(1-naphthyl)methyl
(2-thiophenyl)methyl
2-(2-thiophenyl)ethyl
(2-benzo[b]thiopheneyl)methyl
(2-furyl)methyl
[(5-methyl)furan-2-yl]-methyl
(2-pyridyl)methyl
(3-pyridyl)methyl
(4-pyridyl)methyl;

$R_4$=H, alkyl, carboxyl, carboxymetyhl, carboxyethyl, nitrile, amido, an aromatic system with 0 to 3 substituents selected from, Cl, Br, I, F, $CF_3$, $OCF_3$; or $R_3$=$R_4$ and is selected from carbonyl, —(C=O)—$NR_{10}$—(C=O)—, wherein $R_{10}$ is selected from H, methyl, ethyl;

$R_8$=H, $NHR_9$, alkyl;
$R_9$=methyl, ethyl, isopropyl, sec-butyl
isobutyl
tert-butyl
2-(3-methyl)butyl
cyclopropyl
cyclobutyl
cyclopentyl
cyclohexyl
morpholinyl
methylcyclohexyl
methylcyclopentyl
methylmorpholinyl
hydroxycyclohexyl
hydroxycyclopentyl
benzyl
1-phenylethyl
tetrahydropyran-4-yl
(4-hydroxy)cyclohexyl
1-(1-phenyl)propyl
1-indanyl
1-(1,2,3,4-tetrahydro)naphthyl
1-(2-phenyl)propyl
1-(1-methyl-3-phenyl)propyl
1,2-diphenylethyl
1,3-diphenyl-2-propyl
(4-tert-butyl)benzyl
4-fluorobenzyl
2-(2-para-xylyl)ethyl
(1-naphthyl)methyl
(2-thiophenyl)methyl
2-(2-thiophenyl)ethyl
(2-benzo[b]thiopheneyl)methyl
(2-furyl)methyl
[(5-methyl)furan-2-yl]-methyl
(2-pyridyl)methyl
(3-pyridyl)methyl
(4-pyridyl)methyl.

Compounds such as those described above can be incorporated into a pharmaceutical composition comprising a compound as described above and a pharmaceutically acceptable excipient, carrier or diluent. These pharmaceutical compounds can be administered to a subject in need via depot injection, intramuscular injection, oral application or inhalation. In a preferred embodiment, the dose for human patients is between 0.05 and 22 mg/kg. In a more preferred embodiment, the compounds are used to treat cancers of the colon, liver, pancreas, breast, prostate, brain, throat, bladder, myeloid or lymphoid system.

According to one embodiment of the invention, suitable biologically active variants comprise one or more analogues or derivatives of the compounds described above. Indeed, a single compound, such as those described above, may give rise to an entire family of analogues or derivatives having similar activity and, therefore, usefulness according to the present invention. Likewise, a single compound, such as those described above, may represent a single family member of a greater class of compounds useful according to the present invention. Accordingly, the present invention fully encompasses not only the compounds described above, but analogues and derivatives of such compounds, particularly those identifiable by methods commonly known in the art and recognizable to the skilled artisan.

The compounds disclosed herein may contain chiral centers, which may be either of the (R) or (S) configuration, or may comprise a mixture thereof.

Accordingly, the present invention also includes stereoisomers of the compounds described herein, where applicable, either individually or admixed in any proportions. Stereoisomers may include, but are not limited to, enantiomers, diastereomers, racemic mixtures, and combinations thereof. Such stereoisomers can be prepared and separated using conventional techniques, either by reacting enantiomeric starting materials, or by separating isomers of compounds of the present invention. Isomers may include geometric isomers. Examples of geometric isomers include, but are not limited to, cis isomers or trans isomers across a double bond. Other isomers are contemplated among the compounds of the present invention. The isomers may be used either in pure form or in admixture with other isomers of the compounds described herein.

Various methods are known in the art for preparing optically active forms and determining activity. Such methods include standard tests described herein other similar tests which are well known in the art. Examples of methods that can be used to obtain optical isomers of the compounds according to the present invention include the following: i) physical separation of crystals whereby macroscopic crystals of the individual enantiomers are manually separated. This technique may particularly be used when crystals of the separate enantiomers exist (i.e., the material is a conglomerate), and the crystals are visually distinct; ii) simultaneous crystallization whereby the individual enantiomers are separately crystallized from a solution of the racemate, possible only if the latter is a conglomerate in the solid state; iii) enzymatic resolutions whereby partial or complete separation of a racemate by virtue of differing rates of reaction for the enantiomers with an enzyme; iv) enzymatic asymmetric synthesis, a synthetic technique whereby at least one step of the synthesis uses an enzymatic reaction to obtain an enantiomerically pure or enriched synthetic precursor of the desired enantiomer; v) chemical asymmetric synthesis whereby the desired enantiomer is synthesized from an achiral precursor under conditions that produce asymmetry (i.e., chirality) in the product, which may be achieved using chiral catalysts or chiral auxiliaries; vi) diastereomer separations whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer; vii) first- and second-order asymmetric transformations whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomers; viii) kinetic resolutions comprising partial or complete resolution of a racemate (or of a further resolution of a partially resolved compound) by virtue of unequal reaction rates of the enantiomers with a chiral, non-racemic reagent or catalyst under kinetic conditions; ix) enantiospecif[iota]c synthesis from non-racemic precursors whereby the desired enantiomer is obtained from non-chiral starting materials and where the stereochemical integrity is not or is only minimally compromised over the course of the synthesis; x) chiral liquid chromatography whereby the enantiomers of a racemate are separated in a liquid mobile phase by virtue of their differing interactions with a stationary phase. The stationary phase can be made of chiral material or the mobile phase can contain an additional chiral material to provoke the differing interactions; xi) chiral gas chromatography whereby the racemate is volatilized and enantiomers are separated by virtue of their differing interactions in the gaseous mobile phase with a column containing a fixed non-racemic chiral adsorbent phase; xii) extraction with chiral solvents whereby the enantiomers are separated by virtue of preferential dissolution of one enantiomer into a particular chiral solvent; and xiii) transport across chiral membranes whereby a racemate is placed in contact with a thin membrane barrier. The barrier typically separates two miscible fluids, one containing the racemate, and a driving force such as concentration or pressure differential causes preferential transport across the membrane barrier.

Separation occurs as a result of the non-racemic chiral nature of the membrane which allows only one enantiomer of the racemate to pass through.

Cytokine modulating compounds of the invention may be provided in an enantiomerically enriched form, such as a mixture of enantiomers in which one enantiomer is present in excess (given as a mole fraction or a weight fraction). Enantiomeric excess is understood to exist where a chemical substance comprises two enantiomers of the same compound and one enantiomer is present in a greater amount than the other enantiomer. Unlike racemic mixtures, these mixtures will show a net optical rotation. With knowledge of the specific rotation of the mixture and the specific rotation of the pure enantiomer, the enantiomeric excess (abbreviated "ee") can be determined by known methods. Direct determination of the quantities of each enantiomer present in the mixture is possible with NMR spectroscopy and chiral column chromatography. The compounds of the invention can have a specific degree of enantiomeric purity for a single enantiomer (e.g., at least about 75%, at least about 80%, at least about 85%, at least about 90%, at least about 95%, at least about 96%, at least about 97%, at least about 98%, at least about 99%, or at least about 99.5%).

The compounds described herein can also be in the form of an ester, amide, salt, solvate, prodrug, or metabolite provided they maintain pharmacological activity according to the present invention. Esters, amides, salts, solvates, prodrugs, and other derivatives of the compounds of the present invention may be prepared according to methods generally known in the art, such as, for example, those methods described by J. March, Advanced Organic Chemistry Reactions, Mechanisms and Structure, 4th Ed. (New York: Wiley-Interscience, 1992), which is incorporated herein by reference.

The compounds may also be synthesized with atoms of deuterium, or 13C carbon in certain positions in order to modify properties of stability, or resistance to metabolic enzymes.

Examples of pharmaceutically acceptable salts of the compounds useful according to the invention include acid addition salts. Salts of non-pharmaceutically acceptable acids, however, may be useful, for example, in the preparation and purification of the compounds. Suitable acid addition salts according to the present invention include organic and inorganic acids. Preferred salts include those formed from hydrochloric, hydrobromic, sulfuric, phosphoric, citric, tartaric, lactic, pyruvic, acetic, succinic, fumaric, maleic, oxaloacetic, methanesulfonic, ethanesulfonic, p-toluenesulfonic, benzesulfonic, and isethionic acids. Other useful acid addition salts include propionic acid, glycolic acid, oxalic acid, malic acid, malonic acid, benzoic acid, cinnamic acid, mandelic acid, salicylic acid, and the like. Particular example of pharmaceutically acceptable salts include, but are not limited to, sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxyenzoates, phthalates, sulfonates, xylenesulfonates, phenylacetates, phenylpropionates, phenylbutyrates, citrates, lactates, [gamma]-hydroxybutyrates, glycolates, tartrates, methanesulfonates, propanesulfonates, naphthalene-1-sulfonates, naphthalene-2-sulfonates, and mandelates.

An acid addition salt may be reconverted to the free base by treatment with a suitable base. Preparation of basic salts of acid moieties which may be present on a compound useful according to the present invention may be prepared in a similar manner using a pharmaceutically acceptable base, such as sodium hydroxide, potassium hydroxide, ammonium hydroxide, calcium hydroxide, triethylamine, or the like. Esters of the compounds according to the present invention may be prepared through functionalization of hydroxyl and/or carboxyl groups that may be present within the molecular structure of the compound. Amides and prodrugs may also be prepared using techniques known to those skilled in the art. For example, amides may be prepared from esters, using suitable amine reactants, or they may be prepared from anhydride or an acid chloride by reaction with ammonia or a lower alkyl amine.

Moreover, esters and amides of compounds of the invention can be made by reaction with a carbonylating agent (e.g., ethyl formate, acetic anhydride, methoxyacetyl chloride, benzoyl chloride, methyl isocyanate, ethyl chloroformate, methanesulfonyl chloride) and a suitable base (e.g., 4-dimethylaminopyridine, pyridine, triethylamine, potassium carbonate) in a suitable organic solvent (e.g., tetrahydrofuran, acetone, methanol, pyridine, N,N-dimethylformamide) at a temperature of 0 [deg.]C to 60 [deg.]C. Prodrugs are typically prepared by covalent attachment of a moiety, which results in a compound that is therapeutically inactive until modified by an individual's metabolic system. Examples of pharmaceutically acceptable solvates include, but are not limited to, compounds according to the invention in combination with water, isopropanol, ethanol, methanol, DMSO, ethyl acetate, acetic acid, or ethanolamine.

In the case of solid compositions, it is understood that the compounds used in the compositions of the invention may exist in different forms. For example, the compounds may exist in stable and metastable crystalline forms and isotropic and amorphous forms, all of which are intended to be within the scope of the present invention.

If a compound useful according to the invention is a base, the desired salt may be prepared by any suitable method known to the art, including treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, pyranosidyl acids such as glucuronic acid and galacturonic acid, alpha-hydroxy acids such as citric acid and tartaric acid, amino acids such as aspartic acid and glutamic acid, aromatic acids such as benzoic acid and cinnamic acid, sulfonic acids such a p-toluenesulfonic acid or ethanesulfonic acid, or the like.

If a compound of the invention is an acid, the desired salt may be prepared by any suitable method known to the art, including treatment of the free acid with an inorganic or organic base, such as an amine (primary, secondary or tertiary), an alkali metal or alkaline earth metal hydroxide or the like. Illustrative examples of suitable salts include organic salts derived from amino acids such as glycine and arginine, ammonia, primary, secondary and tertiary amines, and cyclic amines such as piperidine, morpholine and piperazine, and inorganic salts derived from sodium, calcium, potassium, magnesium, manganese, iron, copper, zinc, aluminum and lithium.

The present invention further includes prodrugs and active metabolites of the compounds of the invention. Any of the compounds described herein can be administered as a prodrug to increase the activity, bioavailability, or stability of the compound or to otherwise alter the properties of the compound. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, and/or dephosphorylated to produce the active compound.

A number of prodrug ligands are known. In general, alkylation, acylation, or other lipophilic modification of one or more heteroatoms of the compound, such as a free amine or carboxylic acid residue, reduces polarity and allows passage into cells. Examples of substituent groups that can replace one or more hydrogen atoms on the free amine and/or carboxylic acid moiety include, but are not limited to, the following: aryl; steroids; carbohydrates (including sugars); 1,2-diacylglycerol; alcohols; acyl (including lower acyl); alkyl (including lower alkyl); sulfonate ester (including alkyl or arylalkyl sulfonyl, such as methanesulfonyl and benzyl, wherein the phenyl group is optionally substituted with one or more substituents as provided in the definition of an aryl given herein); optionally substituted arylsulfonyl; lipids (including phospholipids); phosphotidylcholine; phosphocholine; amino acid residues or derivatives; amino acid acyl residues or derivatives; peptides; cholesterols; or other pharmaceutically acceptable leaving groups which, when administered in vivo, provide the free amine and/or carboxylic acid moiety. Any of these can be used in combination with the disclosed compounds to achieve a desired effect.

Pharmaceutical Formulations

While it is possible for the individual compound used in the composition of the present invention to be administered in the raw chemical form, it is preferred for the compounds to be delivered as a pharmaceutical composition. Accordingly, there are provided by the present invention pharmaceutical compositions comprising combinations of compounds as described herein. As such, the compositions of the present invention comprise the pharmaceutically active compounds, as described above, or pharmaceutically acceptable esters, amides, salts, solvates, analogs, derivatives, or prodrugs thereof. Further, the inventive compositions can be prepared and delivered in a variety of combinations. For example, the composition can comprise a single composition containing all of the active ingredients. Alternately, the composition can comprise multiple compositions comprising separate active ingredients but intended to be administered simultaneously, in succession, or in otherwise close proximity of time.

The compounds of the invention can be prepared and delivered together with one or more pharmaceutically acceptable carriers therefore, and optionally, other therapeutic ingredients. Carriers should be acceptable in that they are compatible with any other ingredients of the composition and not harmful to the recipient thereof. A carrier may also reduce any undesirable side effects of the agent. Such carriers are known in the art. See, Wang et a (1980) J. Parent. Drug Assn. 34(6):452-462, herein incorporated by reference in its entirety. Compositions of the present invention may include short-term, rapid-onset, rapid-offset, controlled release, sustained release, delayed release, and pulsatile release compositions, providing the compositions achieve administration of a compound as described herein. See Remington's Pharmaceutical Sciences (18th ed.; Mack Publishing Company, Eaton, Pa., 1990), herein incorporated by reference in its entirety.

Pharmaceutical compositions according to the present invention are suitable for various modes of delivery, including oral, parenteral (including intravenous, intramuscular, subcutaneous, intradermal, intra-articular, intra-synovial, intrathecal, intra-arterial, intracardiac, subcutaneous, intraorbital, intracapsular, intraspinal, intrasternal, and transdermal), topical (including dermal, buccal, and sublingual), vaginal, urethral, and rectal administration. Administration can also be via nasal spray, surgical implant, internal surgical paint, infusion pump, or via catheter, stent, balloon or other delivery device. The most useful and/or beneficial mode of administration can vary, especially depending upon the condition of the recipient and the disorder being treated.

The pharmaceutical compositions may be conveniently made available in a unit dosage form, whereby such compositions may be prepared by any of the methods generally known in the pharmaceutical arts (e.g., shaping into a tablet or forming an aqueous suspension). Pharmaceutical compositions according to the present invention suitable for oral dosage may take various forms, such as tablets, capsules, caplets, and wafers (including rapidly dissolving or effervescing), each containing a predetermined amount of the active agent. The compositions may also be in the form of a powder or granules, a solution or suspension in an aqueous or non-aqueous liquid, and as a liquid emulsion (oil-in-water and water-in-oil). The active agents may also be delivered as a bolus, electuary, or paste. It is generally understood that methods of preparations of the above dosage forms are generally known in the art, and any such method would be suitable for the preparation of the respective dosage forms for use in delivery of the compositions according to the present invention. In one embodiment, compound may be administered orally in combination with a pharmaceutically acceptable vehicle such as an inert diluent or an edible carrier. Oral compositions may be enclosed in hard or soft shell gelatin capsules, may be compressed into tablets or may be incorporated directly with the food of the patient's diet. The percentage of the composition and preparations may be varied; however, the amount of substance in such therapeutically useful compositions is preferably such that an effective dosage level will be obtained.

Hard capsules containing the compound may be made using a physiologically degradable composition, such as gelatin. Soft soft capsules comprise the compound, which may be mixed with water or an oil medium such as peanut oil, liquid paraffin, or olive oil. The compositions of these tablets contain, in addition to the drug, various soluble excipients, such as lactose, powdered sucrose, dextrose, and mannitol. The solid dosage forms of the present invention may optionally be coated, and examples of suitable coating materials include, but are not limited to, cellulose polymers (such as cellulose acetate phthalate, hydroxypropyl cellulose, hydroxypropyl methylcellulose, hydroxypropyl methylcellulose phthalate, and hydroxypropyl methylcellulose acetate succinate), polyvinyl acetate phthalate, acrylic acid polymers and copolymers, and methacrylic resins, zein, shellac, and polysaccharides.

Powdered and granular compositions of a pharmaceutical preparation of the invention may be prepared using known methods. Such compositions may be administered directly to a patient or used in the preparation of further dosage forms, such as to form tablets, fill capsules, or prepare an aqueous or oily suspension or solution by addition of an aqueous or oily vehicle thereto. Each of these compositions may further comprise one or more additives, such as dispersing or wetting agents, suspending agents, and preservatives. Additional excipients (e.g., fillers, sweeteners, flavoring, or coloring agents) may also be included in these compositions. Liquid compositions of the pharmaceutical composition of the invention which are suitable for oral administration may be prepared, packaged, and sold either in liquid form or in the form of a dry product intended for reconstitution with water or another suitable vehicle prior to use. A tablet containing one or more compounds according to the present invention may be manufactured by any standard process readily known to one of skill in the art, such as, for example, by compression or molding, optionally with one or more adjuvant or accessory ingredient. The tablets may optionally be coated or scored and may be formulated so as to provide slow or controlled release of the active agents. Adjuvants or accessory ingredients for use in the compositions of the present invention can include any pharmaceutical ingredient commonly deemed acceptable in the art, such as binders, fillers, lubricants, disintegrants, diluents, surfactants, stabilizers, preservatives, flavoring and coloring agents, and the like. Binders are generally used to facilitate cohesiveness of the tablet and ensure the tablet remains intact after compression. Suitable binders include, but are not limited to: starch, polysaccharides, gelatin, polyethylene glycol, propylene glycol, waxes, and natural and synthetic gums. Acceptable fillers include silicon dioxide, titanium dioxide, alumina, talc, kaolin, powdered cellulose, and microcrystalline cellulose, as well as soluble materials, such as mannitol, urea, sucrose, lactose, dextrose, sodium chloride, and sorbitol. Lubricants are useful for facilitating tablet manufacture and include vegetable oils, glycerin, magnesium stearate, calcium stearate, and stearic acid. Disintegrants, which are useful for facilitating disintegration of the tablet, generally include starches, clays, celluloses, algins, gums, and crosslinked polymers. Diluents, which are generally included to provide bulk to the tablet, may include dicalcium phosphate, calcium sulfate, lactose, cellulose, kaolin, mannitol, sodium chloride, dry starch, and powdered sugar. Surfactants suitable for use in the composition according to the present invention may be anionic, cationic, amphoteric, or nonionic surface active agents. Stabilizers may be included in the compositions to inhibit or lessen reactions leading to decomposition of the active agents, such as oxidative reactions. Solid dosage forms may be formulated so as to provide a delayed release of the active agents, such as by application of a coating. Delayed release coatings are known in the art, and dosage forms containing such may be prepared by any known suitable method. Such methods generally include that, after preparation of the solid dosage form (e.g., a tablet or caplet), a delayed release coating composition is applied. Application can be by methods, such as airless spraying, fluidized bed coating, use of a coating pan, or the like. Materials for use as a delayed release coating can be polymeric in nature, such as cellulosic material (e.g., cellulose butyrate phthalate, hydroxypropyl methylcellulose phthalate, and carboxymethyl ethylcellulose), and polymers and copolymers of acrylic acid, methacrylic acid, and esters thereof.

Solid dosage forms according to the present invention may also be sustained release (i.e., releasing the active agents over a prolonged period of time), and may or may not also be delayed release. Sustained release compositions are known in the art and are generally prepared by dispersing a drug within a matrix of a gradually degradable or hydro lyzable material, such as an insoluble plastic, a hydrophilic polymer, or a fatty compound. Alternatively, a solid dosage form may be coated with such a material.

Compositions for parenteral administration include aqueous and non-aqueous sterile injection solutions, which may further contain additional agents, such as anti-oxidants, buffers, bacteriostats, and solutes, which render the compositions isotonic with the blood of the intended recipient. The compositions may include aqueous and non-aqueous sterile suspensions, which contain suspending agents and thickening agents. Such compositions for parenteral administration may be presented in unit-dose or multi-dose containers, such as, for example, sealed ampoules and vials, and may be stores in a freeze-dried (lyophilized) condition requiring only the addition of the sterile liquid carrier, for example, water (for injection), immediately prior to use. Extemporaneous injection solutions and suspensions may be prepared from sterile powders, granules, and tablets of the kind previously described.

Compositions for rectal delivery of the compositions of the present invention include rectal suppositories, creams, ointments, and liquids. Suppositories may be presented as the active agents in combination with a carrier generally known in the art, such as polyethylene glycol. Such dosage forms may be designed to disintegrate rapidly or over an extended period of time, and the time to complete disintegration can range from a short time, such as about 10 minutes, to an extended period of time, such as about 6 hours.

In certain embodiments, the compounds and compositions disclosed herein can be delivered via a medical device. Such delivery can generally be via any insertable or implantable medical device, including, but not limited to Intratumoural sponges.

Administration of the composition according to the invention comprises administering a single pharmaceutically active compound as described herein; administering a pharmaceutically active compound as described herein with one or more further pharmaceutically active compounds described herein; or administering one or more pharmaceutically active compounds described herein in combination with one or more further pharmaceutically active compounds (i.e., co-administration). Accordingly, it is recognized that the pharmaceutically active compounds in the compositions of the invention can be administered in a fixed combination (i.e., a single pharmaceutical composition that contains both active materials). Alternatively, the pharmaceutically active compounds may be administered simultaneously (i.e., separate compositions administered at the same time). In another embodiment, the pharmaceutically active compounds are administered sequentially (i.e., administration of one or more pharmaceutically active compounds followed by separate administration or one or more pharmaceutically active compounds). One of skill in the art will recognized that the most preferred method of administration will allow the desired therapeutic effect.

Delivery of a therapeutically effective amount of a composition according to the invention may be obtained via administration of a therapeutically effective dose of the composition. The effective amount of the compositions would be expected to vary according to the weight, sex, age, and medical history of the subject. The compound is preferentially administered for a sufficient time period to alleviate the undesired symptoms and the clinical signs associated with the condition being treated. Methods to determine efficacy and dosage are known to those skilled in the art. See, for example, Isselbacher et al. (1996) Harrison's Principles of Internal Medicine 13 ed., 1814-1882, herein incorporated by reference.

The present invention also includes an article of manufacture providing a composition comprising the compounds described herein. The article of manufacture can include a vial or other container that contains a composition suitable for use according to the present invention together with any carrier, either dried or in liquid form. The dosages could be solid forms (e.g., tablets, caplets, capsules, or the like) or liquid forms (e.g., vials), each comprising a single active ingredient, but being provided in blister packs, bags, or the like, for administration in combination.

Specific, non-limiting types of benign tumors that can be treated according to the present invention include hemangiomas, hepatocellular adenoma, cavernous hemangiomas, focal nodular hyperplasia, acoustic neuromas, neurofibroma, bile duct adenoma, bile duct cystanoma, fibroma, lipomas, leiomyomas, mesotheliomas, teratomas, myxomas, nodular regenerative hyperplasia, trachomas, and pyogenic granulomas.

Representative, non-limiting cancers treatable according to the invention include breast cancer, pancreas cancer, skin cancer, bone cancer, prostate cancer, liver cancer, lung cancer, brain cancer, cancer of the larynx, gallbladder, pancreas, rectum, parathyroid, thyroid, adrenal, neural tissue, head and neck, colon, stomach, bronchi, kidneys, basal cell carcinoma, squamous cell carcinoma of both ulcerating and papillary type, metastatic skin carcinoma, osteo sarcoma, Ewing's sarcoma, reticulum cell sarcoma, myeloma, giant cell tumor, small-cell lung tumor, gallstones, islet cell tumor, primary brain tumor, acute and chronic lymphocytic and granulocytic tumors, hairy-cell tumor, adenoma, hyperplasia, medullary carcinoma, pheochromocytoma, mucosal neuromas, intestinal ganglioneuromas, hyperplastic corneal nerve tumor, marfanoid habitus tumor, Wilm's tumor, seminoma, ovarian tumor, leiomyomater tumor, cervical dysplasia and in situ carcinoma, neuroblastoma, retinoblastoma, soft tissue sarcoma, malignant carcinoid, topical skin lesion, mycosis fungoide, rhabdomyosarcoma, Kaposi's sarcoma, osteogenic and other sarcoma, malignant hypercalcemia, renal cell tumor, polycythemia vera, adenocarcinoma, glioblastoma multiforma, leukemias, lymphomas, malignant melanomas, epidermoid carcinomas, and other carcinomas and sarcomas.

EXAMPLES

The present invention will now be described with specific reference to various examples. The following examples are

Example 1

Compound 1

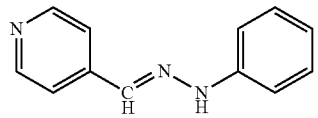 [SMILES: C(=N\Nc1ccccc1)/c1ccncc1]

1-Phenyl-2-(pyridin-4-ylmethylene)hydrazine (1)

4-Pyridinecarboxaldehyde (1.75 g, 16 mmol), phenylhydrazine hydrochloride (2.26 mL, 16 mmol) and triethylamine (1.65 g, 16 mmol) were dissolved in ethanol (50 mL) and heated for 1 h. The reaction mixture was cooled to room temperature. The resulting precipitates were collected and washed with petroleum ether to afford 3.04 g (94%) of 1 as a solid.

$^1$H NMR (400 MHz, DMSO-$d_6$): δ 10.77 (s, 1H), 8.51-8.55 (m, 2H), 7.80 (s, 1H), 7.55-7.59 (m, 2H), 7.22-7.29 (m, 2H), 7.13 (d, 2H), 6.82 (t, 1H).

Example 2

Compound 2

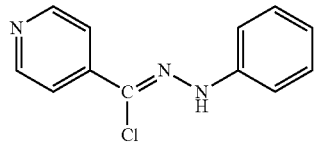 [SMILES: Cl/C(=N\Nc1ccccc1)c1ccncc1]

1-(Chloro(pyridin-4-yl)methylene-2-phenylhydrazine (2)

N-Chlorosuccinimide (2.11 g, 16 mmol) was added portionwise to a solution of compound 1 (2.97 g, 15 mmol) in DMF (15 mL). The reaction mixture was stirred for 10 min at room temperature. The resulting precipitates were collected and washed with petroleum ether to afford 1.82 g (52%) of 2 as a solid.

$^1$H NMR (400 MHz, DMSO-$d_6$): δ 10.31 (s, 1H), 8.65 (d, 2H), 7.82 (d, 2H), 7.43 (d, 2H), 7.28-7.34 (m, 2H), 6.94 (t, 1H).

Example 3

General Procedure for Synthesis of Hydrazones 0.1 mol of the appropriate hydrazine was dissolved in 200 ml ethanol or its hydarzinum salt were used with equivalent amount of Et$_3$N to obtain free hydrazine in solution. 0.1 mol of isonicotinicaldehyde was added to the reaction mixture and was heated at reflux until the reaction was finished (by TLC). The reaction was allowed to cool, a pale yellow solid precipitated andcollected by filtration and recystalized from hot ethanol.

4-(((2,4,6-Trichlorophenyl)hydrazono)methyl)pyridine (3a)[22]

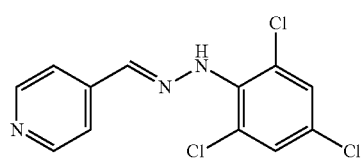 [SMILES: Clc1cc(Cl)c(N/N=C/c2ccncc2)c(Cl)c1]

4-((Phenylhydrazono)methyl)pyridine (3b)[23]

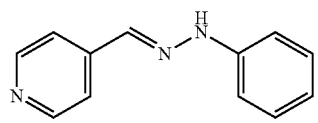 [SMILES: C(=N\Nc1ccccc1)/c1ccncc1]

4-(((4-Chlorophenyl)hydrazono)methyl)pyridine (3c)[23]

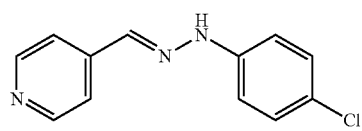 [SMILES: Clc1ccc(N/N=C/c2ccncc2)cc1]

4-(((4-Methoxyphenyl)hydrazono)methyl)pyridine (3d)[24]

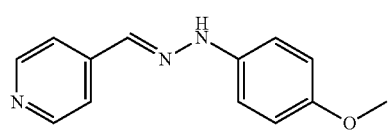 [SMILES: COc1ccc(N/N=C/c2ccncc2)cc1]

4-(((4-Nitrophenyl)hydrazono)methyl)pyridine (3e)[25]

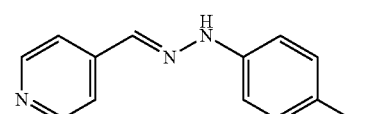

4-((pTolylhydrazono)methyl)pyridine (3f)[24]

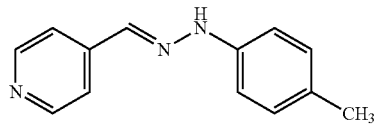 [SMILES: Cc1ccc(N/N=C/c2ccncc2)cc1]

4-(2-(Pyridin-4-ylmethylene)hydrazino)benzonitrile (3g)

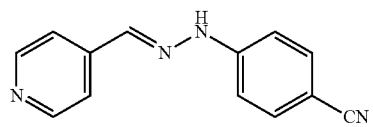 [SMILES: N#Cc1ccc(N/N=C/c2ccncc2)cc1]

Mp. 245° C.; $^1$H NMR (400 MHz, DMSO-$d_6$) 7.23 (d, J=9 Hz, 2H, p-CNPh), 7.64-7.68 (m, 4H, p-CNPh and Py), 7.93 (s, 1H, N=CH), 8.57 (d, J=6 Hz, 2H, Py), 11.39 (s, 1H, NH); $^{13}$C NMR (50 MHz, DMSO-$d_6$) 101.0, 113.1, 120.2, 120.7, 134.1, 137.3, 143.2, 148.4, 149.9; IR (ATR) 3220, 2989, 2938, 2810, 2212 (CN), 1604, 1578, 1542, 1501 (aromatic rings), 1417, 1361, 1278, 996, 907, 829, 813 cm$^{-1}$; MS-FAB: m/z=223 (M-FH)$^+$.

4-(((4-Trifluorophenyl)hydrazono)methyl)pyridine (3h)

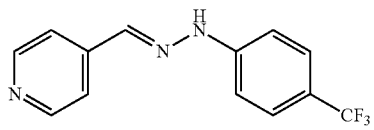

Mp. 239° C.; $^1$H NMR (400 MHz, DMSO-$d_6$) 7.25 (d, J=8 Hz, p-CF$_3$Ph), 7.53-7.63 (m, 4H, p-CF$_3$Ph and Py), 7.89 (s, 1H, N=CH), 8.56 (dd, J$_1$=6 Hz, J$_2$=1 Hz, Py), 11.15 (s, 1H, NH); $^{13}$C NMR (50 MHz, DMSO-$d_6$) 112.6, 120.4, 122.6, 126.8, 126.9, 136.4, 142.8, 148.0, 150.3; IR (ATR) 3229, 3184, 2997, 2947, 1617, 1602, 1578, 1555, 1541, 1510 (aromatic rings), 1420, 1325, 1277, 1158, 1101, 1061, 995, 900, 835 cm$^{-1}$; MS: m/z (%)=266 (100%).

Example 4

General Procedure for Synthesis of Hydrazonyl Chlorides 10 mmol of the appropriate hydrazone was dissolved in a minimum amount of dry DMF (20 ml) at room temperature. 11 mmol of N-chlorosuccinimide (NCS) was added portion-wise to the reaction. The reaction became hot and then the product was precipitated suddenly and reaction was finished (by TLC). The solid was collected by filtration and washed with petroleum ether.

N-(2,4,6-trichlorophenyl)pyridine-4-carbohydrazonoyl chloride (4a)

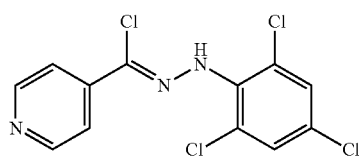 [SMILES: Cl/C(=N\Nc1c(Cl)cc(Cl)cc1Cl)c1ccncc1]

Mp. 215° C.; $^1$H NMR (200 MHz, DMSO-$d_6$) 7.74-7.81 (m, 4H, trichlororAr and Py), 8.66 (d, J=6 Hz, 2H, Py), 9.60 (s, 1H, NH); $^{13}$C NMR (50 MHz, DMSO-$d_6$) 120.1, 128.6, 128.8, 129.4, 136.3, 136.9, 142.9, 150.4; IR (ATR) 3298, 3046, 1632, 1551, 1509, 1487 (aromatic rings), 971, 858, 815 cm$^{-1}$; MS-FAB: m/z=336 (M+H)$^+$.

N-phenylpyridine-4-carbohydrazonoyl chloride (4b)

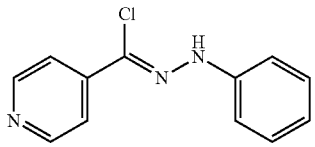 [SMILES: Cl/C(=N\Nc1ccccc1)c1ccncc1]

Mp. 106° C.; $^1$H NMR (400 MHz, DMSO-$d_6$) 6.92 (t, J=7 Hz, 1H, Ph), 7.42-7.25 (m, 4H, Ph), 7.78 (d, J=6 Hz, 2H, Py), 8.63 (d, J=6 Hz, 2H, Py), 10.25 (s, 1H, NH); IR (ATR) 3182, 3057, 1602, 1562, 1541, 1520, 1495 (aromatic rings), 954, 822 cm$^{-1}$; MS-FAB: m/z=232 (M+H)$^+$.

N-(4-chlorophenyl)pyridine-4-carbohydrazonoyl chloride (4c)

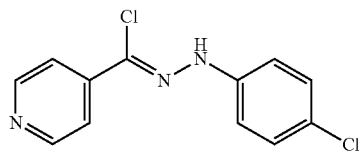 [SMILES: Cl/C(=N\Nc1ccc(Cl)cc1)c1ccncc1]

Mp. 263° C. (decomp.); $^1$H NMR (400 MHz, DMSO-$d_6$) 7.38 (d, J=9 Hz, 2H, p-ClPh), 7.54 (d, J=9 Hz, 2H, p-ClPh), 8.26 (d, J=7 Hz, 2H, Py), 8.83 (d, J=7 Hz, 2H, Py), 11.01 (s, 1H, NH); $^{13}$C NMR (50 MHz, DMSO-$d_6$) 116.8, 118.9, 122.0, 126.6, 129.5, 142.1, 143.2, 148.4; IR (ATR) 3137, 3079, 3046, 2974, 1636, 1605, 1600, 1533, 1483 (aromatic rings), 1402, 1374, 1237, 1202, 1162, 1086, 957, 833, 818 cm$^{-1}$; MS-FAB: m/z=266 (M+H)$^+$.

N-(4-methoxyphenyl)pyridine-4-carbohydrazonoyl chloride (4d)

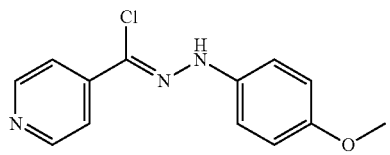 [SMILES: COc1ccc(N/N=C(\Cl)c2ccncc2)cc1]

Mp. 250° C. (decomp.); $^1$H NMR (400 MHz, DMSO-d$_6$) 3.73 (s, 3H, OCH$_3$), 6.94 (d, J=9 Hz, 2H, p-CH$_3$OPh), 7.47 (d, J=9 Hz, 2H, p-CH$_3$OPh), 8.20 (d, J=7 Hz, 2H, Py), 8.78 (d, J=7 Hz, 2H, Py), 10.87 (s, 1H, NH); $^{13}$C NMR (50 MHz, DMSO-d$_6$) 55.7, 115.0, 116.6, 116.7, 121.5, 136.7, 142.6, 149.0, 155.7; IR (ATR) 3152, 2975, 1711, 1635, 1598, 1534, 1488 (aromatic rings), 1233, 955, 850, 822, 805 cm$^{-1}$; MS-FAB: m/z=262 (M+H)$^+$.

N-(4-nitrophenyl)pyridine-4-carbohydrazonoyl chloride (4e)[26]

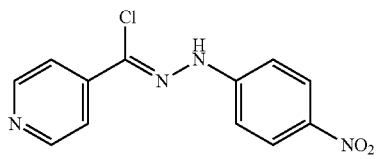 [SMILES: O=[N+]([O-])c1ccc(N/N=C(\Cl)c2ccncc2)cc1]

N-(p-tolyl)pyridine-4-carbohydrazonoyl chloride (4f)

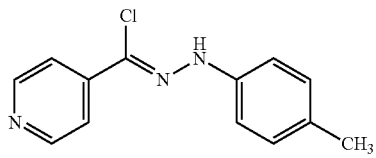 [SMILES: Cc1ccc(N/N=C(\Cl)c2ccncc2)cc1]

Mp. 116° C.; $^1$H NMR (400 MHz, DMSO-d$_6$) 7.09 (d, J=8 Hz, 2H, p-CH$_3$Ph), 7.30 (d, J=8 Hz, 2H, p-CH$_3$Ph), 7.77 (d, J=6 Hz, 2H, Py); 8.61 (d, J=6 Hz, 2H, Py), 10.17 (s, 1H, NH); $^{13}$C NMR (50 MHz, DMSO-d$_6$) 20.7, 114.4, 119.9, 124.0, 130.0, 130.5, 141.6, 150.4; IR (ATR) 3309, 3032, 2917, 1613, 1595, 1566, 1543, 1509 (aromatic rings), 1409, 1317, 1239, 1208, 1136, 996, 949, 816 cm$^{-1}$; MS-FAB: m/z=246 (M+H)$^+$.

N-(4-cyanophenyl)pyridine-4-carbohydrazonoyl chloride (4g)

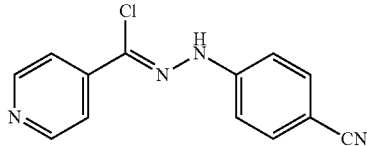 [SMILES: N#Cc1ccc(N/N=C(\Cl)c2ccncc2)cc1]

Mp. 198° C.; $^1$H NMR (400 MHz, DMSO-d$_6$) 7.56 (d, J=8 Hz, 2H, p-CNPh), 7.74 (d, J=9 Hz, 2H, p-CNPh), 7.95 (d, J=6 Hz, 2H, Py), 8.71 (d, J=6 Hz, 2H, Py), 10.88 (s, 1H, NH); $^{13}$C NMR (50 MHz, DMSO-d$_6$): 103.1, 114.9, 120.9, 122.8, 134.0, 143.0, 147.4, 149.0, 151.5; IR (ATR) 3236, 3068, 2219 (CN), 1645, 1606, 1542, 1519, 1487 (aromatic rings), 1451, 1236, 1164, 959, 833, 820 cm$^{-1}$; MS-FAB: m/z=257 (M+H)$^+$.

N-(4-trifluoromethylphenyl)pyridine-4-carbohydrazonoyl chloride (4h)

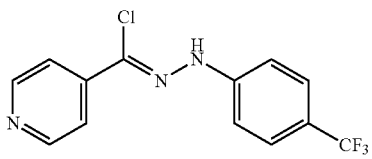

Mp. 140° C.; $^1$H NMR (400 MHz, DMSO-d$_6$) 7.52-7.66 (m, 4H, p-CF$_3$Ph), 7.83 (d, J=5 Hz, 2H, Py), 8.66 (d, J$_1$=5 Hz, Py), 10.65 (s, 1H, NH); $^{13}$C NMR (50 MHz, DMSO-d$_6$) 114.4, 120.3, 121.2, 122.3, 126.8, 126.9, 141.7, 147.1, 150.4; IR (ATR) 3310, 3080, 2911, 1615, 1570, 1528, 1492 (aromatic rings), 1413, 1318, 1061, 999, 953, 831, 818 cm$^{-1}$; MS-FAB: m/z=300 (M+H)$^+$.

Example 5

Compound 5

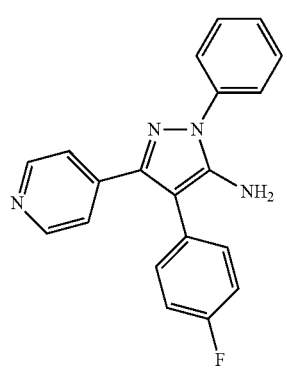 [SMILES: Nc1c(-c2ccc(F)cc2)c(-c2ccncc2)nn1-c1ccccc1]

4-(4-Fluorophenyl)-1-phenyl-3-(pyridine-4-yl)-1H-pyrazol-5-amine (3)

To a solution of diisopropylamine (1.46 mL, 10.4 mmol) in 15 mL abs. THF at −78° C. 4.14 mL n-butyllithium (2.5 M in Hexan) were added dropwise. After stirring for 45 min at −78° C. phenylacetonitrile (0.91 mL, 7.60 mmol) was added. Subsequently, 2 (1.60 g, 6.91 mmol) was added portionwise. The mixture was stirred one hour at −78° C. and one hour at room temperature. After addition of water, the reaction mixture was extracted with ethyl acetate. The combined organic layers were dried (Na$_2$SO$_4$) and the solvent was evaporated. The residue was purified by silica gel chromatography (petroleum ether/ethyl acetate, 6:4) to yield 3 as a solid (0.23 g, 10%).

$^1$H NMR (400 MHz, DMSO-d$_6$): δ 8.49-8.42 (m, 2H), 7.74-7.66 (m, 2H), 7.60-7.16 (m, 9H), 5.21 (s, 2H). MS-ESI (m/z): 331.3 [M+H]$^+$.

The compounds in Examples 6-20 were prepared using methods analogous to those described in Example 5, with exceptions where noted.

Example 6

Compound 6

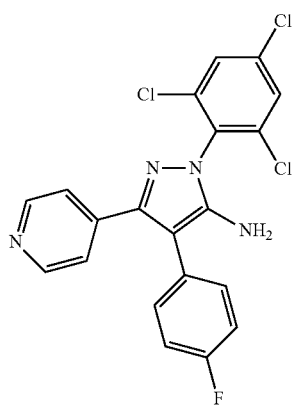 [SMILES: Nc1c(-c2ccc(F)cc2)c(-c2ccncc2)nn1-c1c(Cl)cc(Cl)cc1Cl]

5-(4-Fluorophenyl)-3-(pyridin-4-yl)-1-(2,4,6-trichlorophenyl)-1H-pyrazol-5-amine Yield 35% a pale brown solid, mp. 215° C.; $^1$H NMR (200 MHz, DMSO-d$_6$) 5.53 (br.s, 2H, NH$_2$), 7.67-7.12 (m, 6H, p-FPh and Py), 7.93 (s, 2H, trichloroAr), 8.45 (d, J=6 Hz, 2H, Py); $^{13}$C NMR (50 MHz, DMSO-d$_6$) 99.7, 116.1), 122.0, 129.2, 129.3, 132.0), 133.1, 135.9, 136.2, 141.2, 147.2, 147.5, 149.7, 161.5; IR (ATR) 3451, 3293, 3164 (NH$_2$), 1639 (C=N), 1604, 1573, 1552, 1519 (aromatic rings), 1466, 1212, 972, 833 cm$^{-1}$; MS: m/z (%)=433/435 (100%) (M+H)$^+$, 399, 307, 309, 289; HRMS: (C$_{20}$H$_{12}$Cl$_3$FN$_3$) calculated mass (434.00821), measured mass (434.00583); LC-MS: 433/435 (M+H)$^+$ purity≥96%, HPLC purity≥96%.

Example 7

Compound 7

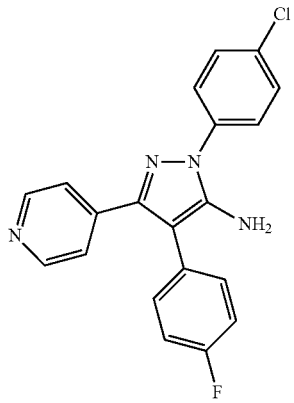 [SMILES: Nc1c(-c2ccc(F)cc2)c(-c2ccncc2)nn1-c1ccc(Cl)cc1]

5-(4-Fluorophenyl)-3-(pyridin-4-yl)-1-(4-chlorophenyl)-1H-pyrazol-5-amine $^1$H NMR (200 MHz, DMSO-d$_6$): δ 8.49-8.42 (m, 2H), 7.79-7.70 (m, 2H), 7.64-7.55 (m, 2H), 7.33-7.20 (m, 6H), 5.33 (s, 2H). MS-EI (m/z): 364.1 (M$^+$), 327.1, 286.1,

Example 8

Compound 8

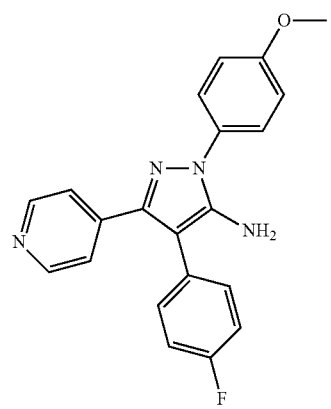 [SMILES: COc1ccc(-n2nc(-c3ccncc3)c(-c3ccc(F)cc3)c2N)cc1]

5-(4-Fluorophenyl)-3-(pyridin-4-yl)-1-(4-methoxyphenyl)-1H-pyrazol-5-amine

Yield 60% a pale brown solid, mp. 200° C.; $^1$H NMR (200 MHz, DMSO-d$_6$) 3.82 (s, 3H, OCH$_3$), 5.10 (br.s, 2H, NH$_2$), 7.31-7.07 (m, 8H, p-CH$_3$OPh, Py and p-FPh), 7.58 (d, J=9 Hz, 2H, p-CH$_3$OPh), 8.45 (d, J=6 Hz, 2H, Py); $^{13}$C NMR (50 MHz, DMSO-d$_6$) 55.8 (OCH$_3$), 102.5, 114.8, 116.0, 121.9, 126.0, 129.4, 131.9, 132.2, 141.4, 145.4, 145.5, 149.9, 158.7, 161.5; IR (ATR) 3450, 3290, 3150 (NH$_2$), 1642 (C=N), 1604, 1573, 1549, 1514 (aromatic rings), 1484, 1216, 1088, 830, 675 cm$^{-1}$; MS: m/z (%)=360 (100%) (M$^+$), 345, 238, 135, 122, 108, 43; HRMS: (C$_{21}$H$_{17}$N$_4$OF) calculated mass (360.138615), measured mass (360.139988); LC-MS: 361 (M+H)$^+$ purity≥99%, HPLC purity≥99%.

Example 9

Compound 9

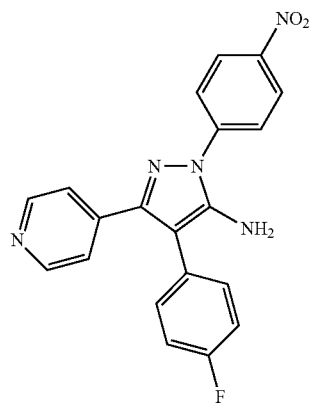 [SMILES: Nc1c(-c2ccc(F)cc2)c(-c2ccncc2)nn1-c1ccc([N+](=O)[O-])cc1]

Example 9

BA516

5-(4-Fluorophenyl)-3-(pyridin-4-yl)-1-(4-nitrophenyl)-1H-pyrazol-5-amine $^1$H NMR (400 MHz, DMSO-d$_6$): δ 8.53-8.47 (m, 2H), 8.43-8.37 (m, 2H), 8.11-8.05 (m, 2H), 7.35-7.24 (m, 6H), 5.58 (s, 2H). MS-FAB (m/z): 376.1 [M+H]$^+$.

Example 10

Compound 10

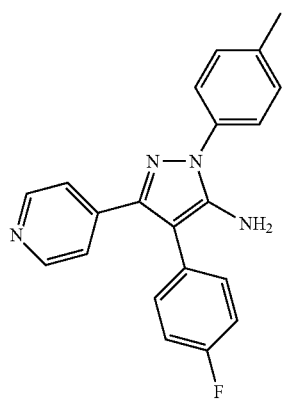 [SMILES: Cc1ccc(-n2nc(-c3ccncc3)c(-c3ccc(F)cc3)c2N)cc1]

Example 10

BA519

5-(4-Fluorophenyl)-3-(pyridin-4-yl)-1-(p-tolyl)-1H-pyrazol-5-amine $^1$H NMR (200 MHz, DMSO-d$_6$): δ 8.48-8.41 (m, 2H), 7.56 (d, 2H), 7.38-7.20 (m, 8H), 5.15 (s, 2H), 2.37 (s, 3H). MS-FAB (m/z): 345.2 [M+H]$^+$.

Example 11

Compound 11

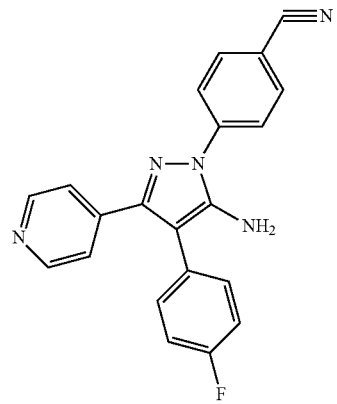 [SMILES: N#Cc1ccc(-n2nc(-c3ccncc3)c(-c3ccc(F)cc3)c2N)cc1]

Example 11

BA529

4-(5-Amino-4-(4-fluorophenyl)-3-(pyridine-4-yl)-1H-pyrazol-1-yl)benzonitrile $^1$H NMR (400 MHz, DMSO-d$_6$): δ 8.50-8.44 (m, 2H), 8.01-7.97 (m, 4H), 7.34-7.21 (m, 6H), 5.49 (s, 2H). MS-ESI (m/z): 356.2 [M+H]$^+$.

Example 12

Compound 12

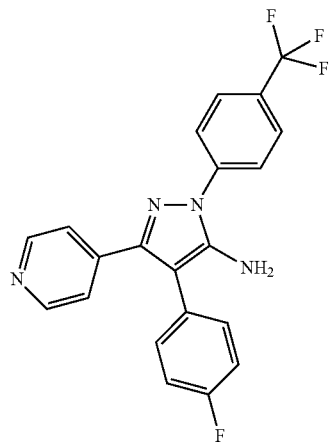 [SMILES: Nc1c(-c2ccc(F)cc2)c(-c2ccncc2)nn1-c1ccc(C(F)(F)F)cc1]

Example 12

BA530

5-(4-Fluorophenyl)-3-(pyridin-4-yl)-1-(4-trifluoromethylphenyl)-1H-pyrazol-5-amine $^1$H NMR (400 MHz, DMSO-d$_6$): δ 8.51-8.44 (m, 2H), 8.04-7.85 (m, 4H), 7.35-7.21 (m, 6H), 5.46 (s, 2H). MS-FAB (m/z): 399.1 [M+H]$^+$.

Example 13

Compound 13

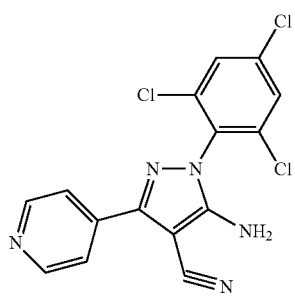 [SMILES: N#Cc1c(-c2ccncc2)nn(-c2c(Cl)cc(Cl)cc2Cl)c1N]

Example 13

BA545

5-Amino-3-(pyridin-4-yl)-1-(2,4,6-trichlorophenyl)-1H-pyrazole-4-carbonitrile $^1$H NMR (400 MHz, DMSO-d$_6$): δ 8.72-8.67 (m, 2H), 8.00 (s, 2H), 7.79-7.76 (m, 2H), 7.22 (s, 2H). MS-ESI (m/z): 366.1 [M+H]$^+$

Example 14

Compound 14

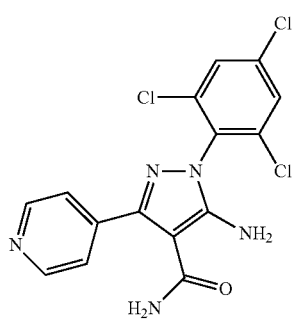 [SMILES: NC(=O)c1c(-c2ccncc2)nn(-c2c(Cl)cc(Cl)cc2Cl)c1N]

Example 14

BA548

5-Amino-3-(pyridin-4-yl)-1-(2,4,6-trichlorophenyl)-1H-pyrazole-4-carboxamide $^1$H NMR (400 MHz, DMSO-d$_6$): δ 8.64-8.60 (m, 2H), 7.97 (s, 2H), 7.60-7.55 (m, 2H), 6.74-6.45 (m, 4H). MS-ESI (m/z): 365.1 [M+H]$^+$

Example 15

Compound 15

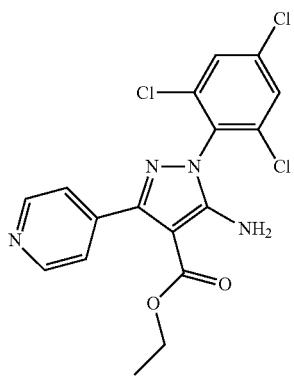 [SMILES: CCOC(=O)c1c(-c2ccncc2)nn(-c2c(Cl)cc(Cl)cc2Cl)c1N]

Example 15

BA549

Ethyl 5-amino-3-(pyridin-4-yl)-1-(2,4,6-trichlorophenyl)-1H-pyrazole-4-carboxylate $^1$H NMR (400 MHz, DMSO-d$_6$): δ 8.62-8.57 (m, 2H), 7.98 (s, 2H), 7.65-7.59 (m, 2H), 6.72 (s, 2H), 4.18 (q, 2H), 1.19 (t, 3H). MS-ESI (m/z): 411.0 [M+H]$^+$.

Example 16

Compound 16

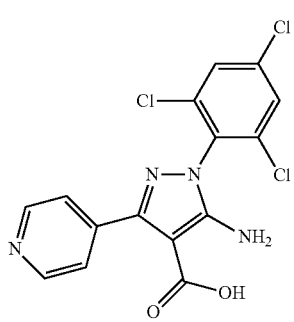 [SMILES: Nc1c(C(=O)O)c(-c2ccncc2)nn1-c1c(Cl)cc(Cl)cc1Cl]

Example 16

BA556

5-Amino-3-(pyridine-4-yl)-1-(2,4,6-trichlorophenyl)-1H-pyrazole-4-carboxylic acid 0.4 mmol of Ethyl 5-amino-3-(pyridin-4-yl)-1-(2,4,6-trichlorophenyl)-1H-pyrazole-4-carb-oxylate (8) was dissolved in 20 ml and 10 ml $H_2O$. 4 eq. (1.6 mmol) of KOH was added to the solution. The reaction was finished after 4 h reflux. The organic solvent was evaporated and the aqueous layer was neutralized in ice bath by adding conc. HCl. A colorless precipitate was filtered and recrystallized from hot ethanol.

Yield 80%, a colorless solid, mp. 208° C.; $^1$H NMR (400 MHz, DMSO-$d_6$) 6.69 (s, 2H, $NH_2$), 7.66 (d, J=5 Hz, 2H, Py), 7.97 (s, 2H, trichloroPh), 8.59 (d, J=5 Hz, 2H, Py); $^{13}$C NMR (50 MHz, DMSO-$d_6$) 91.2, 123.5, 129.0, 131.7, 135.7, 136.0, 140.5, 149.2, 150.3, 153.3, 164.7; IR (ATR) 3450-2500 (HOOC), 3409 ($NH_2$), 3062, 1635 (COOH), 1606, 1553, 1509 (aromatic rings), 1417, 1381, 1276, 1190, 1003, 991, 832 $cm^{-1}$; MS: m/z (%)=383 (100%) $(M+H)^+$, 365, 329, 307, 289, 253, 192; HRMS: ($C_{15}H_9Cl_3N_4O_2$) calculated mass $(M+H)^+$ (382.98639), measured mass (382.98647); HPLC purity≥95%.

Example 17

Compound 17

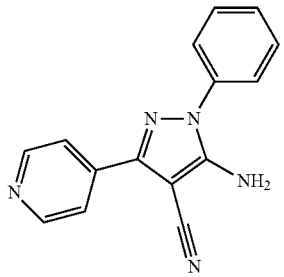 [SMILES: N#Cc1c(-c2ccncc2)nn(-c2ccccc2)c1N]

Example 17

BA557

5-Amino-1-phenyl-3-(pyridine-4-yl)-1H-pyrazole-4-carbonitrile)

$^1$H NMR (400 MHz, DMSO-$d_6$): δ 8.72-8.67 (m, 2H), 7.83-7.79 (m, 2H), 7.62-7.53 (m, 4H), 7.52-7.47 (m, 1H), 6.94 (s, 2H). MS-FAB (m/z): 262.2 $[M+H]^+$.

Example 18

Compound 18

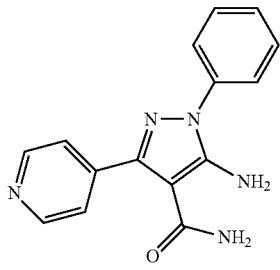 [SMILES: NC(=O)c1c(-c2ccncc2)nn(-c2ccccc2)c1N]

Example 18

BA558

5-Amino-1-phenyl-3-(pyridine-4-yl)-1H-pyrazole-4-carboxamide $^1$H NMR (400 MHz, DMSO-$d_6$): δ 8.68-8.62 (m, 2H), 7.67-7.54 (m, 6H), 7.48-7.42 (m, 1H), 6.35 (s, 2H). MS-FAB (m/z): 280.2 $[M+H]^+$

Example 19

Compound 19

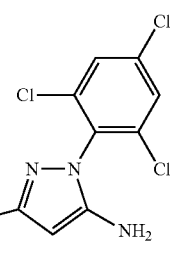

Example 19

BA562

3-(Pyridin-4-yl)-1-(2,4,6-trichlorophenyl)-1H-pyrazol-5-amine $^1$H NMR (400 MHz, DMSO-$d_6$): δ 8.57-8.52 (m, 2H), 7.94-7.89 (m, 2H), 7.70-7.63 (m, 2H), 5.97-5.93 (m, 1H), 5.63 (s, 2H). MS-ESI (m/z): 339.1 $[M+H]^+$.

Example 20

Compound 20

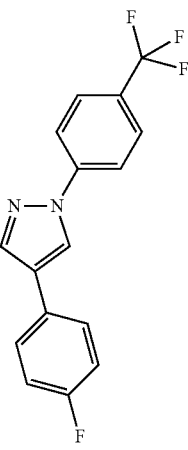

Example 20

BA532

4-(4-(4-Fluorophenyl)-1-(4-trifluoromethyl)phenyl)-1H-pyrazol-3-yl)pyridine 4-(4-trifluoromethylhydrazonomethyl)pyridine was dissolved in 50 mL dried THF. At −78° C. potassium tert-butoxide solution in THF (1.655M) was added dropwise. After stirring at −78° C. for 15 minutes, trans-p-fluoro-ω-nitrostyrene in 6 mL THF was added dropwise. After 15 minutes, TFA was added. The reaction mixture was stirred at −78° C. for 2 hours and warmed to room temperature overnight. The reaction mixture was diluted with water and extracted with EtOAc and the combined organic layer was concentrated in vacuo. The residue was purified by silica gel column chromatography to afford compound 18.

$^1$H NMR (200 MHz, DMSO-$d_6$) 7.27-7.33 (m, 2H, p-FPh), 7.41-7.46 (m, 2H, p-FPh), 7.60 (d, J=6 Hz, 2H, Py), 7.96 (d, J=8 Hz, 2H, p-CF$_3$Ph), 8.22 (d, J=8 Hz, 2H, p-CF$_3$Ph), 8.66 (d, J=6 Hz, 2H, Py), 9.01 (s, 1H, Pyrazol-CH); $^{13}$C NMR (100 MHz, DMSO-$d_6$) 115.6, 118.8, 122.5, 122.8, 126.8, 126.9, 127.6, 129.5, 130.5, 130.6, 141.7, 147.1, 148.5, 161.6; IR (ATR) 3393, 3060, 1617, 1603, 1570, 1541, 1500 (aromatic rings), 1412, 1397, 1320, 1224, 1161, 1110, 1058, 956, 842, 830 cm$^{-1}$; MS: m/z (%)=383 (100%) (M$^+$), 285, 251, 210, 183, 173, 145, 134, 107, 95, 69, 57; HRMS: ($C_{21}H_{13}F_4N_3$) calculated mass (383.10456), measured mass (383.10473); LC-MS: 356 (M+H)$^+$ purity: 95%, HPLC purity: 95%.

Example 21

Compound 21

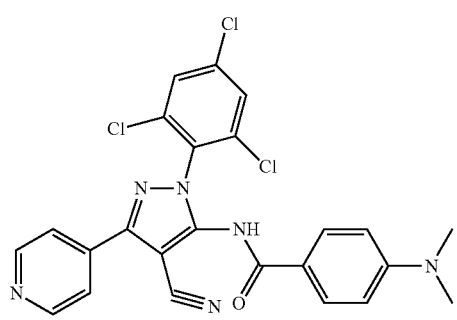 [SMILES: CN(C)c1ccc(C(=O)Nc2c(C#N)c(-c3ccncc3)nn2-c2c(Cl)cc(Cl)cc2Cl)cc1]

Example 21

BA554

N-(4-cyano-3-(pyridin-4-yl)-1-(2,4,6-trichlorophenyl)-1H-pyrazol-5-yl)-4-(dimethylamino)benzamide $^1$H NMR (400 MHz, DMSO-$d_6$): δ 10.85 (s, 1H), 8.81-8.76 (m, 2H), 8.01-7.97 (m, 2H), 7.92-7.87 (m, 2H), 7.73 (d, 2H), 6.74 (d, 2H), 3.00 (s, 6H). MS-ESI (m/z): 511.1 [M+H]$^+$.

Example 22 p38α Enzyme Inhibition Assay

Microtiter plates are coated using a dilution of ATF-2, substrate of p38α. Each step is followed by a threefold washing step. As the substrate doesn't cover the whole surface, blocking buffer is used to capture the free binding sites. In the meantime, the test compounds are diluted using the kinase buffer, which contains ATP [100 μM], phosphatase-inhibitors and the activated p38α. The different dilutions of the test compounds are pipetted on the plate. ATP and the compounds compete for the enzym's binding site. During an incubation time of 60 minutes ATF-2 is dual phosphorylated at Thr 69/71 by p38α kinase depending on its degree of inhibition. Next the first antibody is added into the wells. This antibody binds specifically at dual phosphorylated ATF-2 (Thr 69/71). Secondary antibody, that is conjugated with alkaline phosphatase, binds to the primary antibody. Finally 4-NPP is given in the wells and after an incubation under cover of darkness it is photometrically analysed (405 nm).

Example 23

Effect of Compounds on Cytokine Production by Macrophage

Peritoneal macrophage or spleenocytes (lymphocytes and macrophage) are harvested from donor mice. Cells are placed in culture and stimulated with either LPS or concanavalin A to stimulate macrophage and T-cells respectively. Compounds are added from DMSO stock solutions to a final concentration of 50 μM or less with DMSO not exceeding 1% of total volume. After 72 h, cell supernatant is recovered and the cytokine levels are estimated by ELISA. The effect of compounds on cytokine production is recorded as follows:

Example 24

Treatment of Cancer by Lewis Lung Carcinoma Cells or Cancer of the Pancreas

Figure 2:
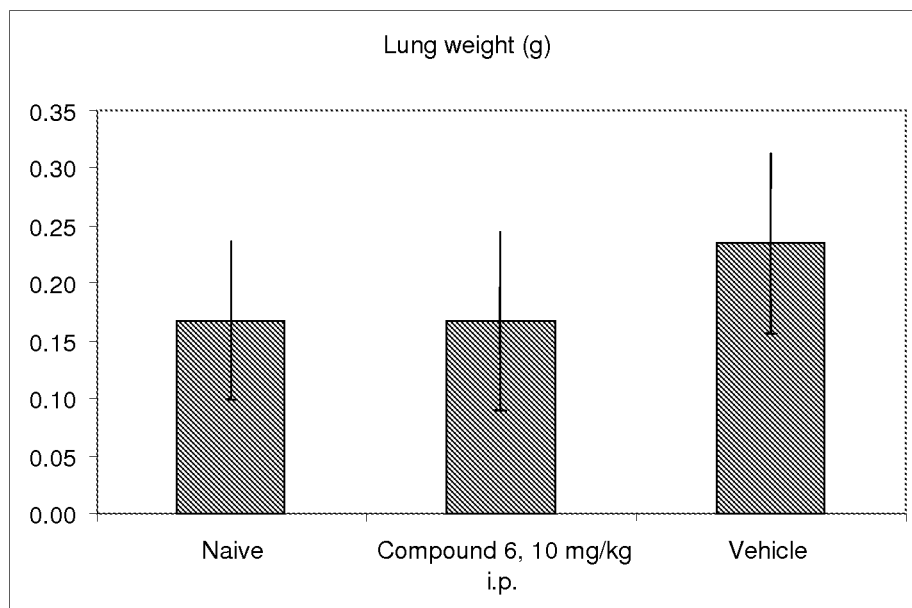
FIG. 2 Lung weight in mice in which 50000 3LL lung carcinoma cells have been injected i.v. at day 0. Tumour growth in lung result in an increase in overall lung weight at termination.
Figure 3:
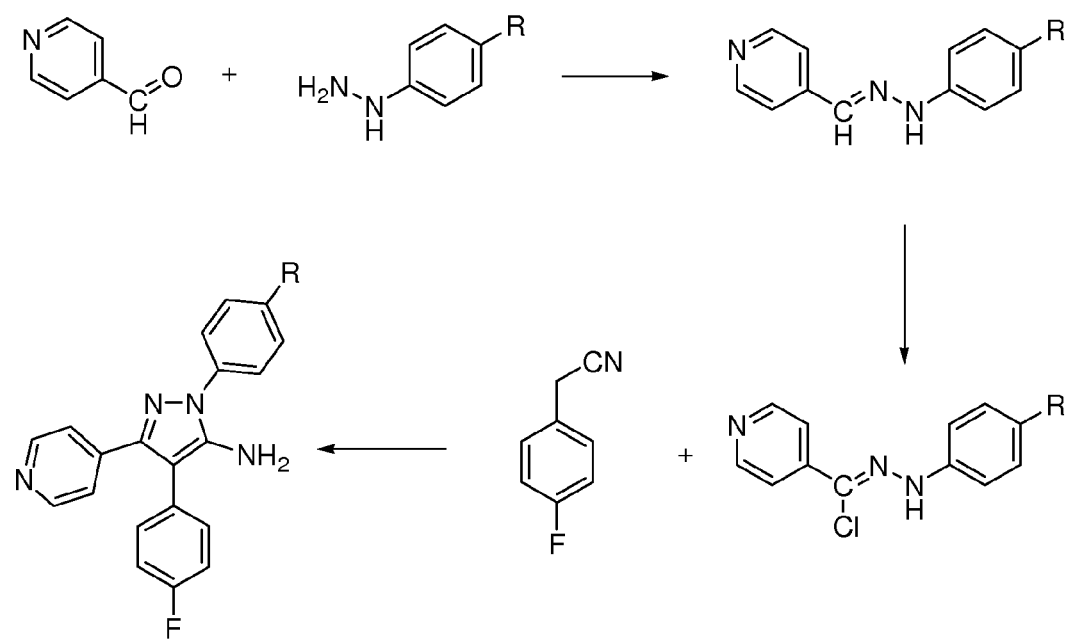
FIG. 3 General synthesis scheme
Figure 4:
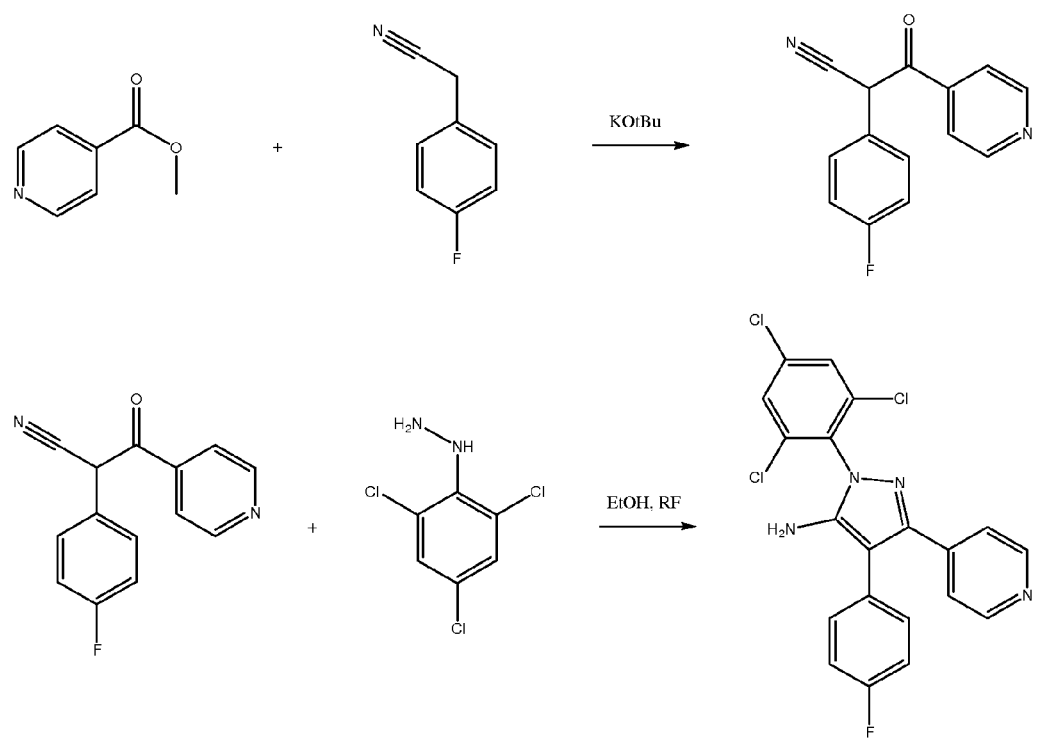
FIG. 4 Alternative general synthesis scheme
Figure 5:
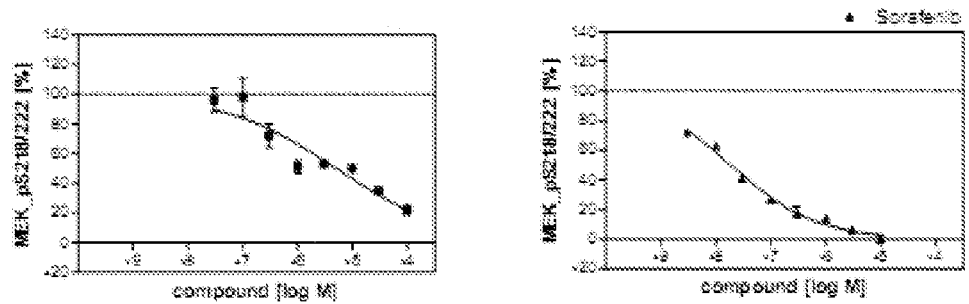
FIG. 5 Compound 6 BRafV600E kinase assay starting from 1E-4M in comparison to BRaf reference inhibitor Sorafenib.
Figure 6:
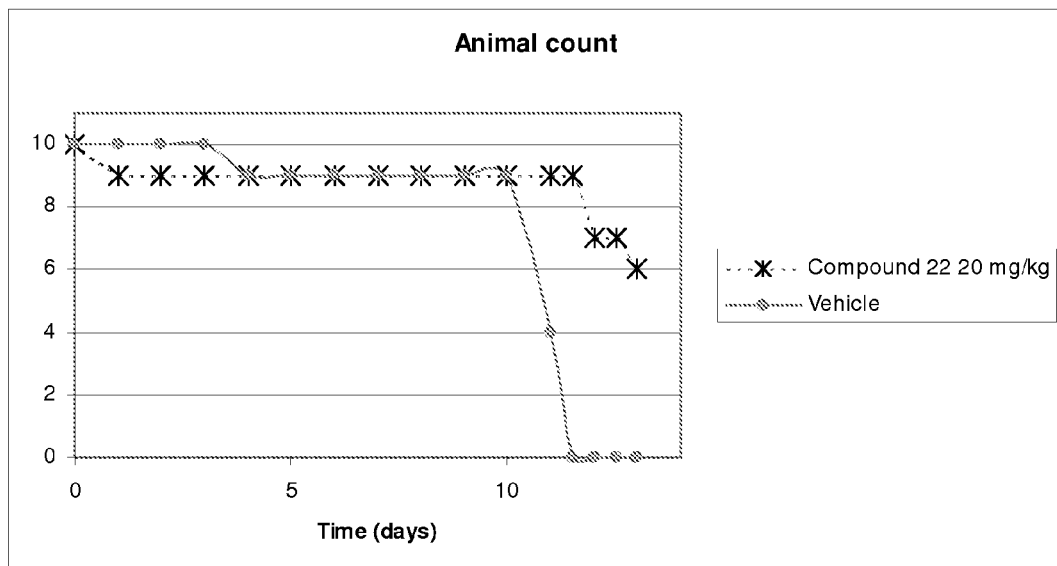
FIG. 6 Effect of Compound 22 on Mastocytoma development.

Lewis Lung Carcinoma Cells (LLC) are cultured by incubation in a medium which is RPMI 1640 (50%) and DMEM (50%) with a final concentration or fetal calf serum of 10%. After culture to the log phase, 5×10$^4$ cells are injected subcutaneously or via i.v. injection in C57BLK6 mice. Mice are treated with substance via intraperitoneal injection. Treatment with the substance compound 6 at a dose of 10 mg/kg p.o. in a vehicle (0.1% Tween 80, 0.5% Hypremellose, 20% PEG 300) once daily results in a reduction in the growth rate of the LLC tumour example data for which are provided in FIGS. 1 and 2.

Example 25

Kinase Assays

FlashPlates from Perkin Elmer (Boston, Mass., USA) with a 50 μl reaction volume are used. The reaction cocktail was pipetted in 4 steps in the following order: 15 μl of ATP solution (in H2O), 20 μl of assay buffer (see below), 5 μl of test sample in 10% DMSO, 10 μl of enzyme/substrate mixture (in H2O). The assay for all enzymes contained 60 mM HEPES-NaOH, pH 7.5, 3 mM $MgCl_2$, 3 mM $MnCl_2$, 3 μM Na-orthovanadate, 1.2 mM DTT, 50 μg/ml PEG20000, 1 μM [γ-33P]-ATP (approx. $8 \times 10^5$ cpm per well), protein kinase (variable amounts; see Table 1), and substrate (variable amounts). Certain assays also contained 1 mM CaCl2, 4 mM EDTA, 5 μg/ml Phosphatidylserine and 1 μg/ml 1.2-Dioleyl-glycerol. The MYLK2, CAMK1D, CAMK2A, CAMK2B, CAMK2D, CAMK4, CAMKK2, DAPK2 and EEF2K assays additionally contained 1 μg/ml Calmodulin and 0.5 mM CaCl2. The PRKG1 and PRKG2 assays additionally contained 1 μM cGMP. Recombinant Protein Kinases: All protein kinases were expressed in Sf9 insect cells or in *E. coli* as recombinant GST-fusion proteins or His-tagged proteins. All kinases were produced from human cDNAs, except JAK2, for which the mouse cDNA was used. Kinases were purified by affinity chromatography using either GSH-agarose (Sigma) or Ni-NTH-agarose (Qiagen). The purity of the protein kinases was examined by SDS-PAGE/coomassie staining. The identity of the protein kinases was checked by mass spectroscopy. Assays were made under license from Chemicon International Inc. for JAK2. The reaction cocktails were incubated at 30° C. for 80 minutes. The reaction was stopped with 50 μl of 2% (v/v) H3PO4, plates were aspirated and washed two times with 200 μl 0.9% (w/v) NaCl. All assays were performed with a BeckmanCoulter Biomek 2000/SL robotic system. Incorporation of 33Pi (counting of "cpm") was determined with a microplate scintillation counter (Microbeta, Wallac).

TABLE 1

Effect of various inhibitors on activity of the enzymes BRAF, Src and VEGFR

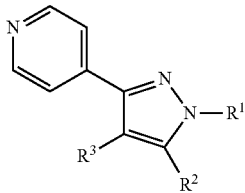

| Comp. | $R^1$ | $R^2$ | $R^3$ | B-Raf V600E (n = 1) | Src (n = 1) | VEGFR-2 (n = 1) |
|---|---|---|---|---|---|---|
| 6 | 2,4,6-trichlorophenyl | $H_2$ | 4-fluorophenyl | 420 | 270 | 29 |

TABLE 1-continued

Effect of various inhibitors on activity of the enzymes BRAF, Src and VEGFR

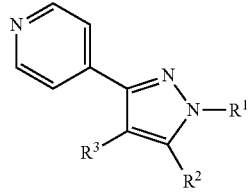

| Comp. | $R^1$ | $R^2$ | $R^3$ | B-Raf V600E (n = 1) | Src (n = 1) | VEGFR-2 (n = 1) |
|---|---|---|---|---|---|---|
| 5 | phenyl | $H_2$ | 4-fluorophenyl | 900 | 52000 | 2400 |
| 7 | 4-chlorophenyl | $H_2$ | 4-fluorophenyl | 800 | 23000 | 1200 |
| 8 | 4-methoxyphenyl | $H_2$ | 4-fluorophenyl | 860 | 23000 | 1900 |
| 9 | 4-nitrophenyl | $H_2$ | 4-fluorophenyl | 1400 | 82000 | 1400 |
| 10 | 4-methylphenyl | $H_2$ | 4-fluorophenyl | 890 | 53000 | 2600 |
| 11 | 4-cyanophenyl | $H_2$ | 4-fluorophenyl | 1700 | >100000 | 1300 |
| 12 | 4-trifluoromethylphenyl | $H_2$ | 4-fluorophenyl | 1500 | 6700 | 2400 |
| 14 | 2,4,6-trichlorophenyl | $H_2$ | carbamoyl | >100000 | 6400 | 31000 |
| 15 | 2,4,6-trichlorophenyl | $H_2$ | ethoxycarbonyl | >100000 | >100000 | >100000 |
| 18 | phenyl | $H_2$ | carbamoyl | 64000 | 19000 | 48000 |
| 16 | 2,4,6-trichlorophenyl | $H_2$ | carboxy | >100000 | 55000 | 43000 |
| 19 | 2,4,6-trichlorophenyl | $H_2$ | H | >100000 | >100000 | 87000 |
| 3a | 2,4,6-trichlorophenyl | | 4-fluorophenyl | 2500 | 2000 | 210 |
| 20 | 4-trifluoromethylphenyl | | 4-fluorophenyl | 2700 | 12000 | 27000 |

TABLE 2

Effect of compound 6 on activity of the mutants of enzymes EGFR, BRAF, Src and VEGFR

| compound | VEGFR-2 (n = 3) | Src (n = 3) | B-Raf wt (n = 1) | B-Raf V600E ((n = 5) | EGFR wt (n = 3) | EGFR T790M (n = 2) | EGFR L858R (n = 3) | EGFR T790M/ L858R (n = 2) |
|---|---|---|---|---|---|---|---|---|
| 6 | 34 | 400 | 270 | 590 | 110 | 2000 | 110 | 1780 |

TABLE 3

Effect of compound 6 on activity of the mutants of enzymes EGFR, and other enzymes relative to Gefitinib.

| No. | Kinase | IC50 (M) Comp. 6 | Gefitinib |
|---|---|---|---|
| 1 | ACK1 | 3.30E−08 | 2.30E−06 |
| 2 | B-RAF V600E | 9.90E−07 | 3.00E−05 |
| 3 | BRK | 6.10E−08 | 9.80E−07 |
| 4 | EGF-R d746-750 | 5.00E−08 | 1.40E−09 |
| 5 | EGF-R d747-749 A750P | 1.70E−07 | 3.10E−09 |
| 6 | EGF-R d747-752 P753S | 1.10E−07 | 2.20E−09 |
| 7 | EGF-R d752-759 | 9.10E−08 | 2.10E−09 |
| 8 | EGF-R G719C | 1.40E−06 | 4.00E−09 |
| 9 | EGF-R G719S | 2.60E−06 | 6.70E−09 |
| 10 | EGF-R L858R | 6.70E−08 | 1.60E−09 |
| 11 | EGF-R L861Q | 1.50E−07 | 2.20E−09 |
| 12 | EGF-R T790M | 3.30E−06 | 2.80E−07 |
| 13 | EGF-R T790M/L858R | 2.80E−06 | 3.10E−06 |
| 14 | EGF-R wt | 2.10E−07 | 3.00E−09 |
| 15 | MINK1 | 9.90E−08 | 1.50E−05 |
| 16 | RIPK2 | 4.10E−08 | 3.80E−08 |

Example 26

Aurora Kinase Assays

Cellular Aurora B kinase assay. In brief, HT29 cells were treated with compounds for 1.5 h in the presence of complete medium (containing 10% FCS) and then substrate dephosphorylation was inhibited using S/T phosphatase inhibitor Calyculin A. After subsequent cell lysis, phosphorylation of cognate Aurora B substrate Histone H3 at S10 was detected using a solid-phase ELISA. Absorption values were converted into percentage phosphorylation using the uninhibited (DMSO-treated) cells as high (=100%) control and cells treated with 1E-5 Staurosporine as low (=0%) control. IC50 values were determined using the programm Prism 5, assuming a sigmoidal dose response.

Example 27

Compound 22, Hydroxy Substituents on the Pyrazole Core

General Procedure for Synthesis Hydroxy Pyrazole Derivatives (71b)

20 mmol of LDA was added to dry THF (30 mL) in a three neck flask and cooled to −78° C. (or LDA was freshly prepared in situ at −78° C.). 14 mmol of ethyl 4-fluorophenyl acetate dissolved in THF (10 mL) was added dropwise and the reaction mixture was stirred for 45 min. 5 mmol of the appropriate hydrazonyl chloride 4a (neat or dissolved in THF) was added slowly to the reaction. After about 1.0 h the reaction was finished and warmed to room temperature. Saturated solution of NH4Cl (100 mL) was added for neutralization the reaction mixture and then followed by adding ethyl acetate (50 mL) and organic phase was separated. The aqueous phase was extracted with ethyl acetate (50 mL) and the combined organic layer was dried over Na2SO4. The solvent was removed under reduced pressure to about 5 mL, left overnight and the product precipitated from the solution. The respective product was filtered off, washed with diethyl ether several times and dried. (yield=35%).

Example 28

Treatment of Mastocytoma Metastases of the Liver and Spleen

Mastocytoma p815 cells are cultured by incubation in a medium which is RPMI 1640 (50%) and DMEM (50%) with a final concentration or fetal calf serum of 10%. After culture to the log phase, 1×105 cells are injected subcutaneously or via i.v. injection in DBA2 mice. Mice are treated with substance 22 via intraperitoneal injection. Treatment with the substance compound 22 at a dose of 20 mg/kg p.o. in a vehicle (sterile saline, 20% PEG 400—substance first dissolved in PEG) once daily results in a reduction in the mortality due to the cancer.

Example 29

Treatment of Amyloidoses

Mice engineered to express amyloid such as the CVN and Tg2576 mice supplied by Charles River are allowed to develop brain pathology up to the age of 6 months. Compound 6 or 22 is dissolved in PEG400 via mechanical agitation and sonication at a concentration of 80 mg/mL. PEG soluitons are administered either directly, or after diluiton in sterile saline containing 1% Tween 80 and administered via s.c injection. For oral administration, compounds are diluted in 5% Tween 80, 10% labrasol, 10% Gelucire (Gatafosse laboratories). Compounds are also administered via food. Compounds are dissolved in an oil 5% phopholipid mix at 25 mg/mL and incorporated into food at 4 mL per 150 g food. After 3 months exposure to substance or Vehicle mice are compared for cognitive parameters including object recognition, water maze performance, and exploration of the open field.

Example 30

Effect of Substances on Cancer Cells

Figure 7:
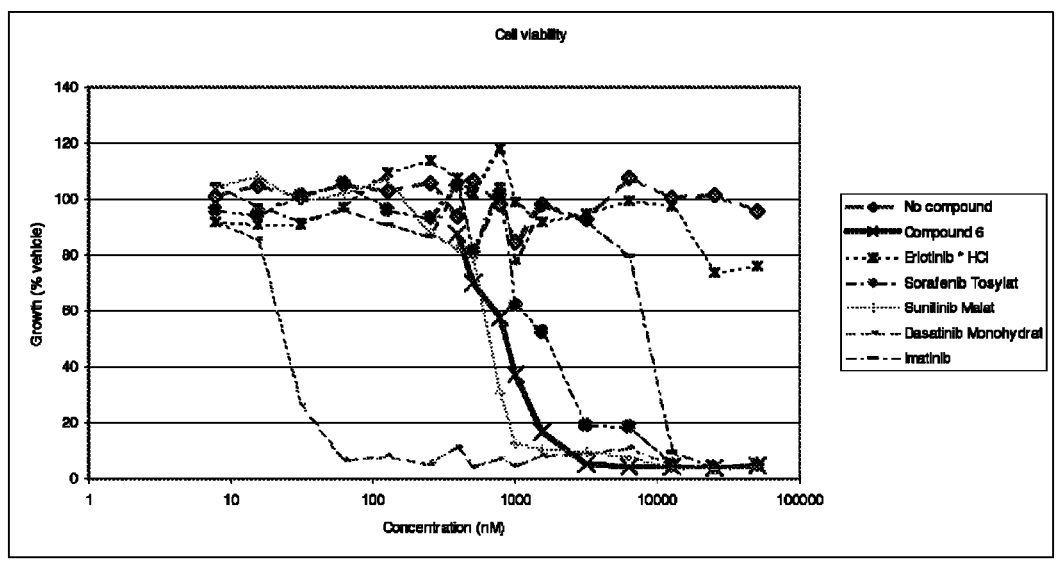
FIG. 7 Effect of compound 6 on p815 Mastocytoma cells vs. reference inhibitor Sorafenib.
Figure 8:
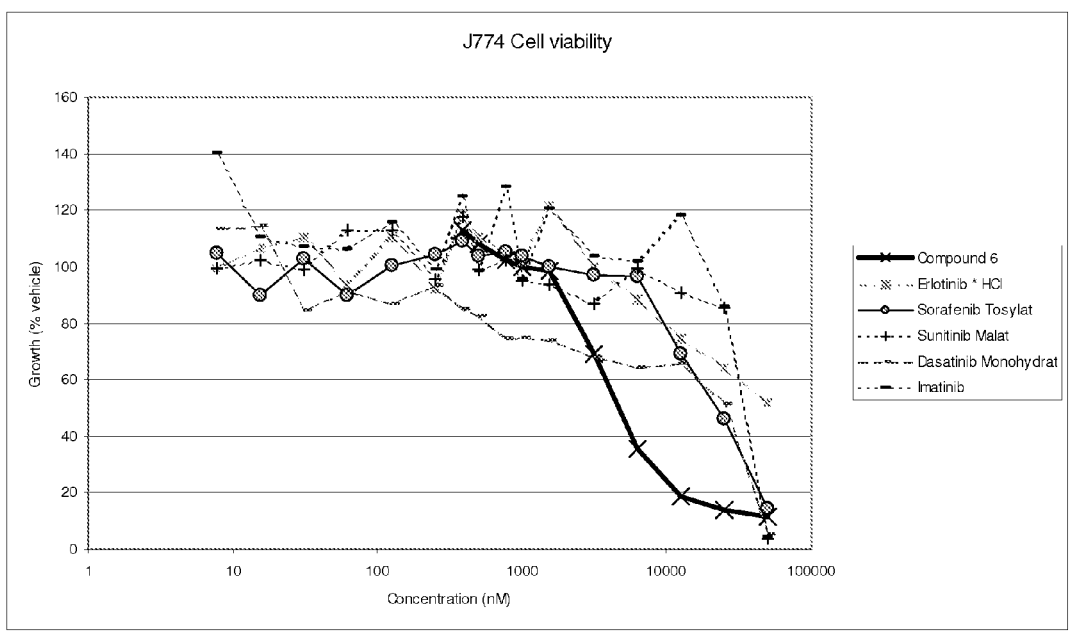
FIG. 8 Effect of compound 6 on J774 murine macrophage cells vs. reference inhibitor Sorafenib.

Murine J774 or p815 cells are cultured by incubation in a medium which is RPMI 1640 (50%) and DMEM (50%) with a final concentration or fetal calf serum of 10%. After culture to the log phase, cells are diluted in medium and mixed with substance at various concentrations using a DMSO stock solution. Cell growth is inhibited in proportion to concentration as indicated in FIGS. 7 and 8.

Other Embodiments

All of the features disclosed in this specification may be combined in any combination. Thus, unless expressly stated otherwise, each feature disclosed is only an example of a generic series of equivalent or similar features.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

ABBREVIATIONS

The following abbreviations were used as noted:
MeOH: methanol
NaHCO$_3$: sodium bicarbonate
K$_2$CO$_3$: potassium carbonate
MS: mass spectrometry DMSO: dimethyl sulfoxide
TLC: thinlayer chromatography
Et$_3$N: triethylamin
EtOAc: ethyl acetate
DCM: dichloromethane
NH$_4$Cl: ammonium chloride
THF: tetrahydrofurane
Na$_2$CO$_3$: sodium carbonate
EDCI: N-Ethyl-N'-(3-dimethylaminopropyl)carbodiimide hydrochloride
DMAP: 4-dimethylamino pyridine

CITATION LIST PATENT LITERATURE

US Patent Documents

US 20010044445. Preparation of azole inhibitors of cytokine production. (2001), Bamaung, et al.

U.S. Pat. No. 7,141,568 Pyrrolo[3,4-c]pyrazole derivatives active as kinase inhibitors, process for their preparation and pharmaceutical compositions comprising them November, 2006 Fancelli et al. 514/234.2

U.S. Pat. No. 3,947,467 3-(5-Nitro-2-imidazolyl) pyrazoles March, 1976 Verge et al.

U.S. Pat. No. 3,526,633 SUBSTITUTED 2,4,5,6-TETRAHYDROPYRROLO(3,4-C)PYRAZOLES September, 1970 Gadekar et al. 546/275.7

U.S. Pat. No. 3,423,414 PYRAZOLOPYRIDINES January, 1969 Blatter 546/119

U.S. Pat. No. 6,436,915 Pyrazole compounds Aug. 20, 2002 Zhang, et al., 514/150

U.S. Pat. No. 4,684,636 Antiandrogenic sulfonylsteroidopyrazoles and processes for preparation method of use and compositions thereof. August, 1987 Christansen et al. 514

U.S. Pat. No. 6,573,270 Pyrazoles Jun. 3, 2003 Banks, et al., 514/274

U.S. Pat. No. 7,897,600 Amino pyrazole compound Dec. 8, 2009 Burkholder, et al., 514/233.2

U.S. Pat. No. 7,638,518 Substituted pyrazole kinase inhibitors Chiu, et al., Oct. 12, 2007 514/253.09

Non-US Patent Documents

Minami, N.; Sato, M.; Hasumi, K.; Yamamoto, N.; Keino, K.; Matsui, T.; Kanada, A.; Ohata, S.; Saito, T.; Sato, S.; Asagarasu, A.; Doi, S.; Kobayashi, M.; Sato, J.; Asano, H. (Teikoku Hormone Mfg. Co., Ltd., Japan). Preparation of aminopyrazole derivatives as p38 mitogen-activated protein (p38MAP) kinase inhibitors. PCT Int. Appl. (2000), WO 2000039116.

Clark, M. T.; Ten Haken, P. Arylhydrazone derivatives useful in biological compositions. Ger. Offen. (1978), DE 2744385.

Kaugaris, G. Pesticidal heterocyclic phenylhydrazone derivates. Ger. Offen. (1972), DE 2149327.

CITATIONS

Non Patent Literature

1. Sachse, A.; Penkova, L.; Noel, G.; Dechert, S.; Varzatskii, O.; Fritsky, I. O.; Meyer, F. Efficient Syntheses of Some Versatile 3,5-Bifunctional Pyrazole Building Blocks. Synthesis 2008, 5, 800-806.
2. Dvorak, C. A.; Rudolph, D. A.; Ma, S.; Carruthers, N. I. Palladium-Catalyzed Coupling of Pyrazole Triflates with Arylboronic Acids. J. Org. Chem. 2005, 70, 4188-4190.
3. Deng, J.; Mani, N., S. Base-Mediated Reaction of Hydrazones and Nitroolefines with a Reversed Regioselectivity: A Novel Synthesis of 1,3,4-Tri-substituted Pyrazoles. Org. Lett. 2008, 10, No. 6, 1307-1310.
4. Kira, M. A.; Abdel-Raeman, M. O.; Gadalla, K. Z., R. Vilsmeier-Haack reaction. III. Cyclization of hydrazones to pyrazoles. Tetrahedron Lett. 1969, 2, 109-110.
5. Stauffer, S. R.; Huang, Y.; Coletta, C. J.; Tedesco, R.; Katzenellenbogen, J. A. Estrogen pyrzaoles: defining the pyrazole core structure and the orientation of substituents in the ligand binding pocket of the estrogen receptor. Bioorg. Med. Chem. 2001, 9, 141-150.
6. Bekhit, A. A.; Abdel-Aziem, T. Design, synthesis and biological evaluation of some pyrazole derivatives as anti-inflammatory-antimicrobial agents. Bioorg. Med. Chem. 2004, 12, 1935-1945.
7. De Paulis, T.; Hemstapat, K.; Chen, Y.; Zhang, Y.; Saleh, S.; Alagille, D.; Baldwin, R. M.; Tamagnan, G. D.; Conn, P. J. Substituent effects of N-(1,3-diphenyl-1H-pyrazol-5-yl) benzamides on positive allosteric modulation of the metabotropic glutamate-5 receptor in rat cortical astrocytes. J. Med. Chem. 2006, 49, 3332-3344.
8. Abu Thaher, B.; Koch, P.; Schattel, V.; Laufer, S. Role of the hydrogen bonding heteroatom-Lys53 interaction between the p38α mitogen-activated protein (MAP) kinase and pyridinyl-substituted 5-membered heterocyclic ring inhibitors. J. Med. Chem. 2009, 52, 2613-2617.
9. Bracht, C.; Hauser, D. R. J.; Schattel, V.; Albrecht, W.; Laufer, S. A., Synthesis and Biological Testing of N-Aminoimidazole-Based p38α MAP Kinase Inhibitors. Chem Med Chem 2010, 5 (7), 1134-1142.
10. Traxler, P.; Furet, P., Strategies toward the design of novel and selective protein tyrosine kinase inhibitors. Pharmacol Ther 1999, 82 (2-3), 195-206.
11. Liu, Y.; Liu, S.; Li, Y.; Song, H.; Wang, Q. Synthesis and biological evaluation of arylhydrazinocyanoacrylates and N-aryl pyrazolecarboxylates. Bioorg. Med. Chem. Lett. 2009, 19, 2953-2956.
12. Makino, K.; Kim, H. S.; Kurasawa, Y. Synthesis of pyrazoles. J. Heterocycl. Chem. 1998, 35, 489-497.
13. Deng, X.; Neelakandha, S. M., Regioselective Synthesis of 1,3,5-Tri- and 1,3,4,5-Tetrasubstituted Pyrazoles from N-Arylhydrazones and Nitroolefins. J. Org. Chem. 2008, 73, 2412-2415.
14. Patel, M. V.; Bell, R.; Majest, S.; Henry, R.; Kolasa, T. Synthesis of 4,5-Diaryl-1H-pyrazole-3-ol Derivatives as Potential COX-2 Inhibitors. J. Org. Chem. 2004, 69, 7058-7065.
15. Peruncheralathan, S.; Khan, T. A.; Ila, H.; Junjappa, H. Regioselective Synthesis of 1-Aryl-3,4-substituted/annulated-5-(methylthio)pyrazoles and 1-Aryl-3-(methylthio)-4,5-substituted/annulated Pyrazoles. J. Org. Chem. 2005, 70, 10030-10035.
16. Silvestri, R.; Cascio, M. G.; La Regina, G.; Piscitelli, A. L.; Brizzi, A.; Pasquinni, S.; Botta, M.; Novellino, E.; Di Marzo, V.; Corelli, F. Synthesis, Cannabinoid Receptor Affinity, and Molecular Modeling Studies of Substituted 1-Aryl-5-(1H-pyrrol-1-yl)-1H-pyrazole-3-carboxamide. J. Med. Chem. 2008, 51, 1560-1576.
17. Goettert, M.; Graeser, R.; Laufer, S. A., Optimization of a nonradioactive immunosorbent assay for p38alpha mitogen-activated protein kinase activity. Anal Biochem 2010, 406 (2), 233-4.
18. Davies, H.; Bignell, G. R.; Cox, C.; Stephens, P.; Edkins, S.; Clegg, S.; Teague, J.; Woffendin, H. et al., Mutations of the BRAF gene in human cancer. Nature 2002, 417 (6892), 949-954.
19. Zhang, H.; Berezov, A.; Wang, Q.; Zhang, G.; Drebin, J.; Murali, R.; Greene, M. I., ErbB receptors: from oncogenes to targeted cancer therapies. *The Journal of Clinical Investigation* 2007, 117 (8), 2051-2058.
20. Verdonk, M. L.; Cole, J. C.; Hartshorn, M. J.; Murray, C. W.; Taylor, R. D., Improved protein-ligand docking using GOLD. *Proteins* 2003, 52 (4), 609-23.
21. Giesecke, H.; Brack, A. Pyridine-4-aldehydephenylhydrazones by pressureless catalytic hydrogenation of 4-cyanopyridine. Eur. Pat. Appl. (1981), EP 22523.
22. Fernandez, A. M.; Troncoso Gonzalez, A. M.; Guzman Chozas, M. p-Nitrophenylhydrazones of pyridinealdehydes. Spectroscopy studies. *Journal of Molecular Structure* 1986, 143, 557-560.
23. Repetto E, Yoon I S, Zheng H, Kang D E. Presenilin 1 regulates epidermal growth factor receptor turnover and signaling in the endosomal-lysosomal pathway. J Biol. Chem. 2007 Oct. 26; 282(43):31504-16
24. Li T, Wen H, Brayton C, Das P, Smithson L A, Fauq A, Fan X, Crain B J, Price D L, Golde T E, Eberhart C G, Wong P C Epidermal growth factor receptor and notch pathways participate in the tumor suppressor function of gamma-secretase. J Biol. Chem. 2007 Nov. 2; 282(44):32264-73.
25. Lei W, Hsueh-Cheng C, Wenjuan W, Bin L, Zuolei X, Xinsheng Y, Weiwei M, Shuwen D, Yi Z., Epidermal growth factor receptor is a preferred target for treating Amyloid-β-induced memory loss Published online Sep. 27, 2012, doi: 10.1073/pnas. 1208011109 PNAS.

The contents of each patent and non-patent reference are incorporated herein by reference in their entirety.

The invention claimed is:

1. A compound according to Formula 1 wherein:

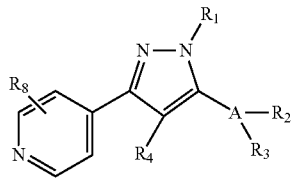

Formula 1

$R_1$=is phenyl substituted with 0 to 3 substituents selected from alkyl of 1 to 5 carbons, halogen, nitrile, alkoxy, nitro;
A=N;
$R_2$ and $R_3$ are independently selected from either no atom in the case of A=O, and hydrogen, methyl, ethyl, isopropyl, sec-butyl
isobutyl
tert-butyl
2-(3-methyl)butyl
cyclopropyl
cyclobutyl
cyclopentyl
cyclohexyl
methylcyclohexyl
methylcyclopentyl
hydroxycyclohexyl
hydroxycyclopentyl
benzyl
1-phenylethyl
(4-hydroxy)cyclohexyl
1-(1-phenyl)propyl
1-(1,2,3,4-tetrahydro)naphthyl
1-(2-phenyl)propyl
1-(1-methyl-3-phenyl)propyl
1,2-diphenylethyl
1,3-diphenyl-2-propyl
(4-tert-butyl)benzyl
4-fluorobenzyl
2-(2-para-xylyl)ethyl
(1-naphthyl)methyl
(2-thiophenyl)methyl
2-(2-thiophenyl)ethyl
(2-benzo[b]thiophenyl)methyl
(2-furyl)methyl
[(5-methyl)furan-2-yl]-methyl
(2-pyridyl)methyl
(3-pyridyl)methyl
(4-pyridyl)methyl;
$R_4$=carboxyl, carboxymetyhl, carboxyethyl, nitrile, amido, phenyl with 0 to 3 substituents selected from, Cl, Br, I, F, $CF_3$, $OCF_3$;
or $R_3$=$R_4$ and is selected from carbonyl, —(C=O)—$NR_{10}$—(C=O)—, wherein $R_{10}$ is selected from H, methyl, ethyl;
$R_8$=H;
$R_9$=methyl, ethyl, isopropyl, sec-butyl
isobutyl
tert-butyl
2-(3-methyl)butyl
cyclopropyl
cyclobutyl
cyclopentyl
cyclohexyl
methylcyclohexyl
methylcyclopentyl
hydroxycyclohexyl
hydroxycyclopentyl
benzyl
1-phenylethyl
(4-hydroxy)cyclohexyl
1-(1-phenyl)propyl
1-(1,2,3,4-tetrahydro)naphthyl
1-(2-phenyl)propyl
1-(1-methyl-3-phenyl)propyl
1,2-diphenylethyl
1,3-diphenyl-2-propyl
(4-tert-butyl)benzyl
4-fluorobenzyl
2-(2-para-xylyl)ethyl
(1-naphthyl)methyl
(2-thiophenyl)methyl
2-(2-thiophenyl)ethyl
(2-benzo[b]thiopheneyl)methyl
(2-furyl)methyl
[(5-methyl)furan-2-yl]-methyl
(2-pyridyl)methyl
(3-pyridyl)methyl
(4-pyridyl)methyl.

2. A compound according to claim 1 wherein $R_4$ is phenyl substituted with 0 to 3 substituents selected from Cl, Br, I, F, $CF_3$, $OCF_3$.

3. A compound according to claim 2 wherein $R_4$ is 4-Fluorophenyl and $R^1$ is 2,4,6-trichlorophenyl.

4. A pharmaceutical composition comprising a compound as claimed in claim 1 and a pharmaceutically acceptable excipient, carrier or diluent.

5. A compound according to Formula 3 wherein:

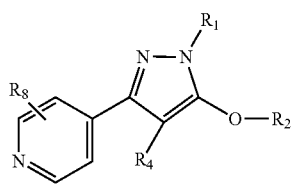

Formula 3

$R_1$ = is phenyl with 0 to 4 substituents selected from alkyl of 1 to 5 carbons, halogens, nitrile, alkoxy, nitro;
$R_2$ is independently selected from methyl, ethyl, isopropyl,
  sec-butyl
  isobutyl
  tert-butyl
  2-(3-methyl)butyl
  cyclopropyl
  cyclobutyl
  cyclopentyl
  cyclohexyl
  methylcyclohexyl
  methylcyclopentyl
  hydroxycyclohexyl
  hydroxycyclopentyl
  benzyl
  1-phenylethyl
  (4-hydroxy)cyclohexyl
  1-(1-phenyl)propyl
  1-(1,2,3,4-tetrahydro)naphthyl
  1-(2-phenyl)propyl
  1-(1-methyl-3-phenyl)propyl
  1,2-diphenylethyl
  1,3-diphenyl-2-propyl
  (4-tert-butyl)benzyl
  4-fluorobenzyl
  2-(2-para-xylyl)ethyl
  (1-naphthyl)methyl
  (2-thiophenyl)methyl
  2-(2-thiophenyl)ethyl
  (2-benzo[b]thiophenyl)methyl
  (2-furyl)methyl
  [(5-methyl)furan-2-yl]-methyl
  (2-pyridyl)methyl
  (3-pyridyl)methyl
  (4-pyridyl)methyl;
$R_4$ = H, alkyl, carboxyl, carboxymetyhl, carboxyethyl, nitrile, amido, phenyl with 0 to 3 substituents selected from, Cl, Br, I, F, $CF_3$, $OCF_3$;
or $R_3=R_4$ and is selected from carbonyl, —(C═O)—$NR_{10}$—(C═O)—, wherein $R_{10}$ is selected from H, methyl, ethyl;
$R_8$ = H, $NHR_9$, alkyl;
$R_9$ = methyl, ethyl, isopropyl, sec-butyl
  isobutyl
  tert-butyl
  2-(3-methyl)butyl
  cyclopropyl
  cyclobutyl
  cyclopentyl
  cyclohexyl
  methylcyclohexyl
  methylcyclopentyl
  hydroxycyclohexyl
  hydroxycyclopentyl
  benzyl
  1-phenylethyl
  (4-hydroxy)cyclohexyl
  1-(1-phenyl)propyl
  1-(1,2,3,4-tetrahydro)naphthyl
  1-(2-phenyl)propyl
  1-(1-methyl-3-phenyl)propyl
  1,2-diphenylethyl
  1,3-diphenyl-2-propyl
  (4-tert-butyl)benzyl
  4-fluorobenzyl
  2-(2-para-xylyl)ethyl
  (1-naphthyl)methyl
  (2-thiophenyl)methyl
  2-(2-thiophenyl)ethyl
  (2-benzo[b]thipheneyl)methyl
  (2-furyl)methyl
  [(5-methyl)furan-2-yl]-methyl
  (2-pyridyl)methyl
  (3-pyridyl)methyl
  (4-pyridyl)methyl.

6. The compound of claim 1, wherein the compound is:
4-(4-Fluorophenyl)-1-phenyl-3-(pyridine-4-yl)-1H-pyrazol-5-amine;
5-(4-Fluorophenyl)-3-(pyridin-4-yl)-1-(2,4,6-trichlorophenyl)-1H-pyrazol-5-amine;
5-(4-Fluorophenyl)-3-(pyridin-4-yl)-1-(4-chlorophenyl)-1H-pyrazol-5-amine;
5-(4-Fluorophenyl)-3-(pyridin-4-yl)-1-(4-methoxyphenyl)-1H-pyrazol-5-amine;
5-(4-Fluorophenyl)-3-(pyridin-4-yl)-1-(4-nitrophenyl)-1H-pyrazol-5-amine;
5-(4-Fluorophenyl)-3-(pyridin-4-yl)-1-(p-tolyl)-1H-pyrazol-5-amine;
4-(5-Amino-4-(4-fluorophenyl)-3-(pyridine-4-yl)-1H-pyrazol-1-yl)benzonitrile;
5-(4-Fluorophenyl)-3-(pyridin-4-yl)-1-(4-trifluoromethylphenyl)-1H-pyrazol-5-amine;
5-Amino-3-(pyridin-4-yl)-1-(2,4,6-trichlorophenyl)-1H-pyrazole-4-carbonitrile;
5-Amino-3-(pyridin-4-yl)-1-(2,4,6-trichlorophenyl)-1H-pyrazole-4-carboxamide;
Ethyl 5-amino-3-(pyridin-4-yl)-1-(2,4,6-trichlorophenyl)-1H-pyrazole-4-carboxylate;
5-Amino-3-(pyridine-4-yl)- 1-(2,4,6-trichlorophenyl)-1H-pyrazole-4-carboxylic acid;
5-Amino-1-phenyl-3-(pyridine-4-yl)-1H-pyrazole-4-carbonitrile); or
5-Amino-1-phenyl-3-(pyridine-4-yl)-1H-pyrazole-4-carboxamide.

* * * * *